US012558685B2

(12) United States Patent
Wilson et al.

(10) Patent No.: US 12,558,685 B2
(45) Date of Patent: Feb. 24, 2026

(54) FLUIDIC DEVICES INVOLVING SIGNAL GENERATION AT CONVERGING LIQUID FRONTS

(71) Applicant: Trustees of Tufts College, Medford, MA (US)

(72) Inventors: Daniel J. Wilson, Mapleville, RI (US); Charles R. Mace, Winchester, MA (US)

(73) Assignee: Trustees of Tufts College, Medford, MA (US)

( * ) Notice: Subject to any disclaimer, the term of this patent is extended or adjusted under 35 U.S.C. 154(b) by 989 days.

(21) Appl. No.: 17/252,503

(22) PCT Filed: Jun. 19, 2019

(86) PCT No.: PCT/US2019/037941
§ 371 (c)(1),
(2) Date: Dec. 15, 2020

(87) PCT Pub. No.: WO2019/246229
PCT Pub. Date: Dec. 26, 2019

(65) Prior Publication Data
US 2021/0268500 A1 Sep. 2, 2021

Related U.S. Application Data

(60) Provisional application No. 62/688,718, filed on Jun. 22, 2018.

(51) Int. Cl.
*B01L 3/00* (2006.01)
*C12Q 1/28* (2006.01)
(Continued)

(52) U.S. Cl.
CPC .......... *B01L 3/502715* (2013.01); *C12Q 1/28* (2013.01); *C12Q 1/32* (2013.01);
(Continued)

(58) Field of Classification Search
CPC ................................................ B01L 3/502715
See application file for complete search history.

(56) References Cited

U.S. PATENT DOCUMENTS

| 5,262,067 | A | 11/1993 | Wilk et al. |
| 5,846,438 | A | 12/1998 | Pall et al. |

(Continued)

FOREIGN PATENT DOCUMENTS

| WO | WO 2017/123668 A1 | 7/2017 |
| WO | WO 2018/099922 A1 | 6/2018 |

OTHER PUBLICATIONS

U.S. Appl. No. 17/252,511, filed Dec. 15, 2020, Mace et al.

(Continued)

*Primary Examiner* — Randy Boyer

(74) *Attorney, Agent, or Firm* — Wolf, Greenfield & Sacks, P.C.

(57) ABSTRACT

Articles and methods involving fluidic devices are generally provided. In some embodiments, a fluidic device comprises a first layer comprising first and second regions that are disconnected from each other in the first layer and a second layer comprising a channel in fluidic communication with the first and second regions. The device may also comprise a third layer comprising a channel in fluidic communication with the first and second regions. One or more portions of a channel and/or one or more reagents may comprise a reagent. In some embodiments, a method comprises flowing two or more fluid samples towards each other through a channel. The fluids may meet at an interface and/or may react at an interface.

20 Claims, 19 Drawing Sheets

4000

(51) Int. Cl.
  *C12Q 1/32* (2006.01)
  *C12Q 1/46* (2006.01)
(52) U.S. Cl.
  CPC ............ *C12Q 1/46* (2013.01); *B01L 2200/10*
    (2013.01); *B01L 2300/12* (2013.01); *B01L*
      *2300/126* (2013.01); *B01L 2300/168*
      (2013.01); *B01L 2400/0406* (2013.01)

(56) References Cited

U.S. PATENT DOCUMENTS

| | | | |
|---|---|---|---|
| 6,036,659 | A | 3/2000 | Ray et al. |
| 6,274,041 | B1 | 8/2001 | Williamson et al. |
| 6,494,230 | B2 | 12/2002 | Chow |
| 6,623,860 | B2 | 9/2003 | Hu et al. |
| 6,739,576 | B2 | 5/2004 | O'Connor et al. |
| 7,318,912 | B2 | 1/2008 | Pezzuto et al. |
| 2002/0187072 | A1 | 12/2002 | Karp |
| 2002/0187560 | A1* | 12/2002 | Pezzuto .............. B01F 35/7182 |
| | | | 422/504 |
| 2006/0280029 | A1 | 12/2006 | Garstecki et al. |
| 2007/0092975 | A1 | 4/2007 | Potyrailo et al. |
| 2008/0241962 | A1 | 10/2008 | Wang |
| 2011/0123398 | A1* | 5/2011 | Carrilho .............. F16K 99/0001 |
| | | | 422/68.1 |
| 2012/0009662 | A1 | 1/2012 | Shen et al. |
| 2012/0322086 | A1 | 12/2012 | Garnier et al. |
| 2013/0130226 | A1 | 5/2013 | Lim et al. |
| 2014/0295472 | A1 | 10/2014 | Shevkoplyas et al. |
| 2015/0087079 | A1 | 3/2015 | Coffey et al. |
| 2016/0038939 | A1 | 2/2016 | Min et al. |
| 2016/0090588 | A1 | 3/2016 | Lofquist et al. |
| 2018/0200677 | A1 | 7/2018 | Lee et al. |
| 2019/0391130 | A1 | 12/2019 | Murray et al. |
| 2021/0263027 | A1 | 8/2021 | Mace et al. |
| 2024/0337653 | A1 | 10/2024 | Mace et al. |

OTHER PUBLICATIONS

PCT/US2019/037941, Aug. 29, 2019, International Search Report and Written Opinion.
International Search Report and Written Opinion for PCT/US2019/037941 mailed Aug. 29, 2019.
[No Author Listed], Simple spot check. GE Healthcare Life Sciences. Mar. 2010:2 pages [last accessed Apr. 25, 2017].
[No Author Listed], Vivid™M Plasma Separation Membrane. Pall Corporation. https://shop.pall.com/us/en/medical/advanced-materials/diagnostics/vivid-plasma-separation-membrane-zidgri78lls [last accessed Mar. 4, 2021].
Berry et al., Measurement of the hematocrit using paper-based microfluidic devices. Lab Chip. Oct. 7, 2016;16(19):3689-94. doi: 10.1039/c61c00895j. Epub Sep. 7, 2016.
Carrilho et al., Understanding wax printing: a simple micropatterning process for paper-based microfluidics. Anal Chem. Aug. 15, 2009;81(16):7091-5. doi: 10.1021/ac901071p.
Cheng et al., Paper-based ELISA. Angew Chem Int Ed Engl. Jun. 28, 2010;49(28):4771-4. doi: 10.1002/anie.201001005.
Dechiara et al., An Open Software Platform for the Automated Design of Paper-Based Microfluidic Devices. Sci Rep. Nov. 24, 2017;7(1):16224. doi: 10.1038/s41598-017-16542-8.
Deraney et al., Multiplexed, Patterned-Paper Immunoassay for Detection of Malaria and Dengue Fever. Anal Chem. Jun. 21, 2016;88(12):6161-5. doi: 10.1021/acs.analchem.6b00854. Epub Jun. 1, 2016.
Fernandes et al., Beyond Wicking: Expanding the Role of Patterned Paper as the Foundation for an Analytical Platform. Anal Chem. Jun. 6, 2017;89(11):5654-5664. doi: 10.1021/acs.analchem.6b03860. Epub Apr. 26, 2017.
Fernandes et al., Comparison of three indirect immunoassay formats on a common paper-based microfluidic device architecture. Anal Methods. Jun. 2016;8:5204-11.

Fernandes et al., Fabrication of Three-dimensional Paper-based Microfluidic Devices for Immunoassays. J Vis Exp. Mar. 9, 2017;(121):55287. doi: 10.3791/55287.
Gao et al., Ultrasensitive paper based nucleic acid detection realized by three-dimensional DNA-AuNPs network amplification. Biosens Bioelectron. Jun. 15, 2017;92:529-535. doi: 10.1016/j.bios.2016.10.068. Epub Oct. 27, 2016.
Kim et al., Simple, miniaturized blood plasma extraction method. Anal Chem. Dec. 3, 2013;85(23):11501-8. doi: 10.1021/ac402735y. Epub Nov. 7, 2013.
Leuthold et al., New microfluidic-based sampling procedure for overcoming the hematocrit problem associated with dried blood spot analysis. Anal Chem. Feb. 17, 2015;87(4):2068-71. doi: 10.1021/ac503931g. Epub Jan. 30, 2015.
Li et al., A perspective on paper-based microfluidics: Current status and future trends. Biomicrofluidics. Mar. 2012;6(1):11301-1130113. doi: 10.1063/1.3687398. Epub Mar. 2, 2012.
Luckham et al., Bioactive paper dipstick sensors for acetylcholinesterase inhibitors based on sol-gel/enzyme/gold nanoparticle composites. Analyst. Aug. 2010;135(8):2028-35. doi: 10.1039/c0an00283f. Epub Jun. 3, 20100.
Mace et al., Manufacturing prototypes for paper-based diagnostic devices. Microfluid Nanofluid. 2014;16:801-9. doi: 10.1007/s10404-013-1314-6.
Martinez et al., Programmable diagnostic devices made from paper and tape. Lab Chip. Oct. 7, 2010;10(19):2499-504. doi: 10.1039/c01c00021c. Epub Jul. 30, 2010.
Pollock et al., A paper-based multiplexed transaminase test for low-cost, point-of-care liver function testing. Sci Transl Med. Sep. 19, 2012;4(152):152ra129. doi: 10.1126/scitranslmed.3003981.
Riccardi et al., Covalent interlocking of glucose oxidase and peroxidase in the voids of paper: enzyme-polymer "spider webs". Chem Commun (Camb). Feb. 11, 2016;52(12):2593-6. doi: 10.1039/c6cc00037a. Epub Jan. 11, 2016.
Rosypal et al., Evaluation of a novel dried blood spot collection device (HemaSpot™) to test blood samples collected from dogs for antibodies to Leishmania infantum. Vet Parasitol. Sep. 15, 2014;205(1-2):338-42. doi: 10.1016/j.vetpar.2014.07.031. Epub Aug. 12, 2014.
Schneider et al., NIH Image to ImageJ: 25 years of image analysis. Nat Methods. Jul. 2012;9(7):671-5. doi: 10.1038/nmeth.2089.
Schonhorn et al., A device architecture for three-dimensional, patterned paper immunoassays. Lab Chip. Dec. 2, 20141;14(24):4653-8. doi: 10.1039/c4lc00876f. Epub Oct. 10, 2014.
Wilson et al., Reconfigurable Pipet for Customized, Cost-Effective Liquid Handling. Anal Chem. Sep. 5, 2017;89(17):8656-8661. doi: 10.1021/acs.analchem.7b02556. Epub Aug. 11, 2017.
Zhang et al., A dye-assisted paper-based point-of-care assay for fast and reliable blood grouping. Sci Transl Med. Mar. 15, 2017;9(381):eaaf9209. doi: 10.1126/scitranslmed.aaf9209. Epub Mar. 15, 2017.
[No Author Listed], Processing of Dried Blood Spots Standard Operating Procedure. ACTG/IMPAACT Lab Tech Committee. Mar. 19, 2012: 20 pages.
[No Author Listed], Who Manual for HIV Drug Resistance Testing Using Dried Blood Spot Specimens. World Health Organization. Jul. 2012: 26 pages.
Baillargeon et al., Patterned Dried Blood Spot Cards for the Improved Sampling of Whole Blood. ACS Meas Sci Au. Feb. 16, 2022;2(1):31-38. doi: 10.1021/acsmeasuresciau.1c00031. Epub Sep. 17, 2021.
Rottinghaus et al., Comparison of Ahlstrom grade 226, Munktell TFN, and Whatman 903 filter papers for dried blood spot specimen collection and subsequent HIV-1 load and drug resistance genotyping analysis. J Clin Microbiol. Jan. 2013;51(1):55-60. doi: 10.1128/JCM.02002-12. Epub Oct. 17, 2012.
Ryona et al., A Book-Type Dried Plasma Spot Card for Automated Flow-Through Elution Coupled with Online SPE-LC-MS/MS Bioanalysis of Opioids and Stimulants in blood. Anal Chem. Nov. 15, 2016;88(22):11229-11237. doi: 10.1021/acs.analchem.6b03691. Epub Nov. 2, 2016.
U.S. Appl. No. 18/742,297, filed Jun. 13, 2024, Mace et al.
U.S. Appl. No. 18/705,119, filed Apr. 26, 2024, Mace et al.

(56)          References Cited

OTHER PUBLICATIONS

Morbioli et al., Improving Sample Distribution Homogeneity in Three-Dimensional Microfluidic Paper-Based Analytical Devices by Rational Device Design. Anal Chem. May 2, 2017;89(9):4786-4792. doi: 10.1021/acs.analchem.6b04953. Epub Apr. 19, 2017.

* cited by examiner

1000

2000

2000

3000

4000

A

Physiological range: 5–15mM

0mM (water)

5mM 7.5mM

10mM 12.5mM

15mM g. ox. = glucose oxidase

HRP = horseradish peroxidase

KI = potassium iodide alg. = sodium alginate ppm Fe(III)  0        100        200        300        400        500 acetylthiocholine →            ← Ellman's reagent

U/mL AChE    0        25        30        35        40        45 sample addition sample distribution reagent storage interface formation transparent laminate original design modified design 2.5 µm 15 µm 25 µm

FLUIDIC DEVICES INVOLVING SIGNAL GENERATION AT CONVERGING LIQUID FRONTS

RELATED APPLICATIONS

This application is a national stage filing under 35 U.S.C. § 371 of international PCT application, PCT/US2019/037941, filed Jun. 19, 2019, and entitled "Fluidic Devices Involving Signal Generation at Converging Liquid Fronts", which claims priority under 35 U.S.C. § 119(e) to U.S. Provisional Application No. 62/688,718, filed Jun. 22, 2018, and entitled "Fluidic Devices Involving Signal Generation at Converging Liquid Fronts", which are incorporated herein by reference in their entirety for all purposes.

FIELD

Articles and methods involving fluidic devices are generally provided.

SUMMARY

Articles and methods involving fluidic devices are generally provided. The subject matter disclosed herein involves, in some cases, interrelated products, alternative solutions to a particular problem, and/or a plurality of different uses of one or more systems and/or articles.

Some aspects relate to fluidic devices. In some embodiments, a fluidic device comprises a first layer comprising a first channel, a second layer comprising first and second regions in fluidic communication with the first channel, and a third layer comprising a second channel in fluidic communication with the first and second regions. The first and second regions are disconnected from each other in the second layer. The first layer is disposed on the second layer. The second layer is disposed on the third layer. At least one of the first layer, second layer, and third layer comprises a porous material.

In some embodiments, a fluidic device comprises a first layer comprising first and second regions and a second layer comprising a channel in fluidic communication with the first and second regions. The first and second regions are disconnected from each other in the first layer. The first layer is disposed on the second layer. At least one of the first and second layers comprises a porous material. At least one of the first region, the second region, and the channel comprises a first reagent.

Some aspects relate to methods. In some embodiments, a method comprises flowing a fluid sample through a first channel in a first layer, flowing a first portion of the fluid sample through a first region in a second layer, flowing a second portion of the fluid sample through a second region in the second layer, flowing the first portion of the fluid sample into a second channel in a third layer, flowing the second portion of the fluid sample into the second channel in the third layer or into a third channel intersecting the second channel, and allowing the first and second portions of the fluid sample to meet at an interface. The first and second regions are disconnected from each other in the second layer. At least one of the first layer, second layer, and third layer comprises a porous material.

In some embodiments, a method comprises flowing, in a first direction, a first fluid comprising a first reagent through a first channel, flowing, in a second direction, a second fluid sample comprising a second reagent through the first channel or a second channel intersecting the first channel, wherein the first and second directions are different, and reacting the first reagent with the second reagent to form a detectable signal. The detectable signal forms at an interface between a fluid front of the first fluid and a fluid front of the second fluid.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
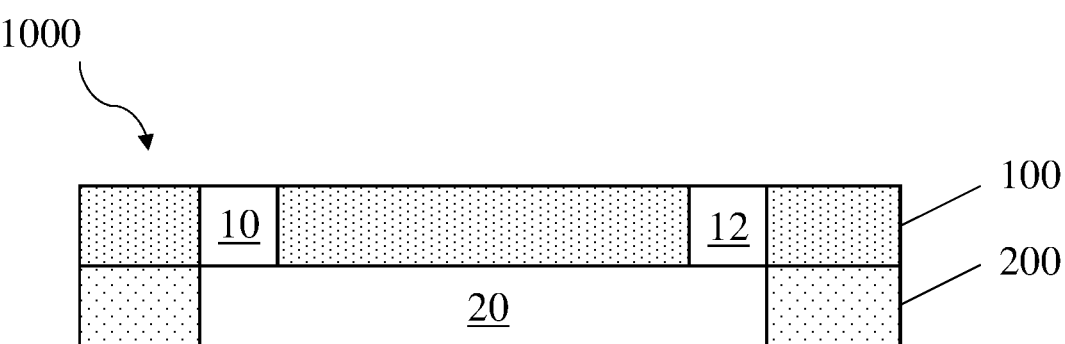
FIG. 1A shows one non-limiting example of a device comprising two layers, according to some embodiments.

Articles and methods related to fluidic devices are generally provided. In some embodiments, an article described herein has utility for performing reactions at interfaces between fluids and/or portions of fluid samples. For example, the fluid front (e.g., fluid/air interface) of a first fluid flowing towards an intersection of a channel may meet with the fluid front of a second fluid flowing towards the intersection, and components of the two fluids may react at the intersection. Performing reactions at interfaces between fluids and/or portions of fluid samples may be beneficial for a variety of reasons. For example, reactions performed at interfaces between fluids and/or portions of fluid samples may generate reaction products that are localized at the interface for an appreciable period of time. The interface may comprise a higher concentration of the reaction products than those that are present in other regions of fluidic devices in which reactions may occur (e.g., regions comprising stored, dried reagents that are configured to react with fluids flowing thereover). A higher concentration of reaction products may facilitate detection of reaction products at lower concentrations and/or of reaction products that provide a weak signal. In some embodiments, a higher concentration of reaction products facilitates comparison of the extent of the reaction forming the reaction products.

Another advantage that may be associated with performing reactions at interfaces between fluids and/or portions of fluid samples is the possibility of performing multiple reactions with a single fluid sample and/or portion of a fluid sample. A single fluid sample may be capable of forming interfaces with multiple fluid samples, and so may be capable of undergoing multiple reactions. In some embodiments, three or more fluids and/or three or more portions of fluid samples may form interfaces with each other within a relatively small portion of a fluidic device (e.g., at an intersection of three or more channels). In such embodiments, the interfaces between the fluids and/or portions of fluid samples may be relatively close together, and so the reactions between the fluids and/or portions of fluid samples may occur in relatively close proximity. Close proximity of the reactions may facilitate comparisons between one or more features of the reactions (e.g., intensity of the signals provided by reaction products formed), which may facilitate comparisons between the fluids and/or portions of fluid samples. This may be beneficial for comparing reactions involving control samples with reactions involving samples to be analyzed.

In some embodiments, the fluidic devices and/or methods described herein are employed to form reaction products that are localized to a thin layer, such as a thin layer that forms an interface between two fluids and/or two portions of a fluid sample. The thin layer may appear to be a line with a relatively thin thickness when the fluidic device is viewed from the top or bottom. The formation of a detectable signal (e.g., a reaction product) in a shape that appears to be a line may have a variety of advantages. For instance, it may be similar to the format in which detectable signals are produced in commonly-available and commonly-used fluidic devices and so may be easily interpretable and/or familiar.

The fluidic devices described herein may be employed to form detectable signals that appear to be lines that indicate the presence or absence of certain species that may otherwise be challenging to detect by observing the presence or absence of lines (e.g., analytes that do not react with a species, such as an antibody, that may be immobilized in a fluidic device to form a line; analytes that react with a species that may be immobilized in a fluidic device to form a line, but which is prohibitively complicated or expensive to obtain).

It should be understood that, unless otherwise indicated, references to first and second fluids (and/or third fluids, fourth fluids, etc.) may refer to portions of a single initial fluid sample that had previously been split to form the first and second portions thereof and/or may refer to first and second fluids that were not previously portions of a single fluid sample (e.g., a first fluid sample to be analyzed within the fluidic device and a second fluid sample that comprises a reagent configured to react with the first fluid sample to form a detectable signal). Unless otherwise indicated, references to fluids may refer to fluid samples, fluids that are not samples, and/or portions of fluid samples. Non-limiting examples of fluids and fluid samples are provided in further detail below.

Figure 1B:
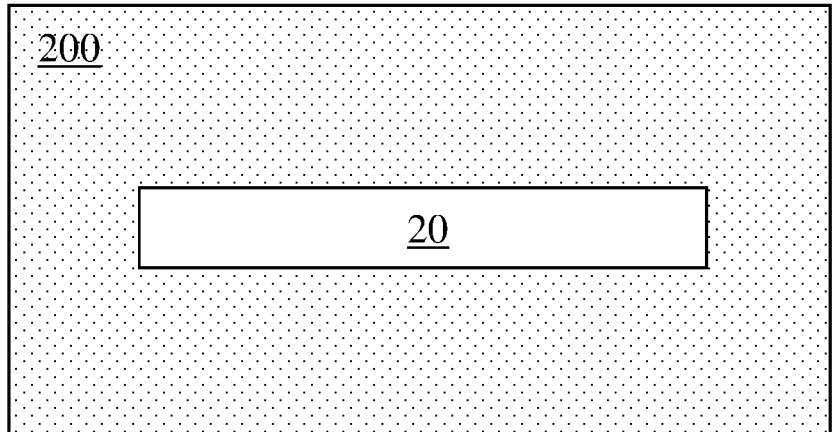
FIG. 1B shows a bottom view of the fluidic device shown in FIG. 1A, according to some embodiments.

In some embodiments, a fluidic device (e.g., a fluidic device in which one or more reactions may be performed at one or more interfaces) may comprise one or more layers (e.g., two or more layers). One or more of these layers may be a layer comprising two or more regions disconnected from each other in the layer. One or more of these layers may be a layer comprising a channel. The layer comprising the channel may be in fluidic communication with the disconnected regions (which may be channels, in some embodiments), and may fluidically connect the disconnected regions. In some embodiments, the disconnected regions are not in fluidic communication with each other through the first layer. FIG. 1A shows one non-limiting example of a device comprising these layers. In FIG. 1A, a device 1000 comprises a first layer 100 and a second layer 200. The first layer 100 comprises a first region 10 and a second region 12 which are disconnected from each other in the first layer. The second layer comprises a channel 20 which is in fluidic communication with the first region 10 and the second region 12. FIG. 1B shows a bottom view of the fluidic device shown in FIG. 1A showing the second layer 200 and the channel 20 therein.

As shown illustratively in FIG. 1A, the first layer (e.g., the layer comprising the regions disconnected from each other in the layer) is directly disposed on the second layer (e.g., the layer comprising the channel) and/or the channel in the second layer is positioned directly below the disconnected regions in the first layer. However, in other embodiments, a fluidic device may comprise the two layers shown in FIG. 1A, and may further comprise one or more intervening layers positioned between the first layer shown in FIG. 1A and the second layer shown in FIG. 1A. In some embodiments, a fluidic device may comprise the two layers shown in FIG. 1A and may further comprise one or more layers disposed on the first layer and/or on which the second layer is disposed. It should also be understood that a device may comprise a layer comprising two or more regions that are disconnected from each other in the layer having a structure other than that shown in FIG. 1A and/or may comprise a layer comprising a channel having a structure other than that shown in FIG. 1A. For instance, a layer may comprise more than two regions that are disconnected from each other, the regions may occupy volume fractions of the layer other than that shown in FIG. 1A, and/or may have relative sizes other than that shown in FIG. 1A (e.g., the regions may be the same size or may have different sizes). As further examples, a layer may comprise a channel occupying a volume fraction of the layer other than that shown in FIG. 1A, may comprise more than one channel, may comprise a channel extending beyond one or more regions in a layer to which it is adjacent, may comprise a channel not in fluidic communication with one or more regions in a layer to which it is adjacent, and/or may comprise a channel having a different relative size with respect to regions in a layer to which it is adjacent.

As used herein, when a layer is referred to as being "on" or "disposed on" another layer, it can be directly disposed on the layer, or an intervening layer also may be present. A layer that is "directly on" or "directly disposed on" another layer is positioned with respect to the layer such that no intervening layer is present.

As described above, a fluidic device described herein may comprise a layer comprising a channel (e.g., a channel in a layer in a fluidic device comprising more than one layer, as is shown in FIG. 1A; a channel in fluidic communication with one or more disconnected regions, as is shown in FIG. 1A). A method may comprise flowing two fluids and/or two portions of a fluid sample through the channel in different directions. In some embodiments, the fluids may flow by capillary action. The fluids or portions of fluid samples may flow towards each other and/or may flow such that they meet at an interface, intersection, or other suitable area. The interface may be an interface between the fluid fronts of the fluids. Once the fluids meet at an interface, the fluids may cease flowing (e.g., since the channel has been filled), and the components within the fluids may undergo a chemical and/or biological reaction or interaction at the interface, e.g., by diffusion of the sample components.

Figure 2A:
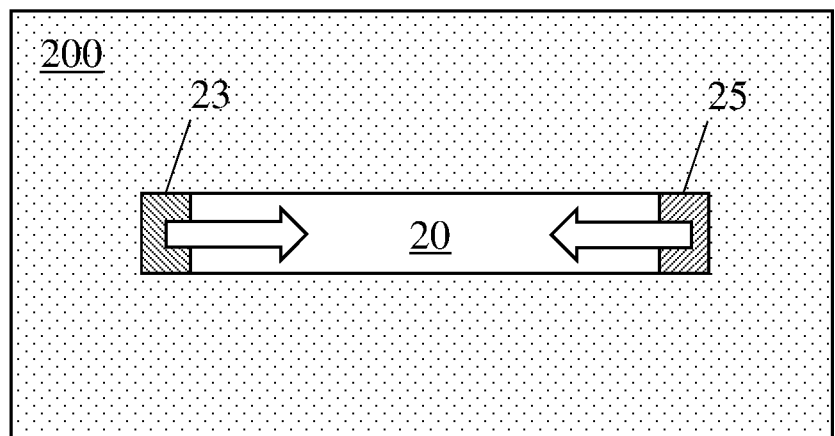
FIGS. 2A-2C show one non-limiting embodiment of a method in which two fluids flow through a channel in different directions and then meet at an interface between the fluid fronts of the fluids, according to some embodiments.
Figure 2B:
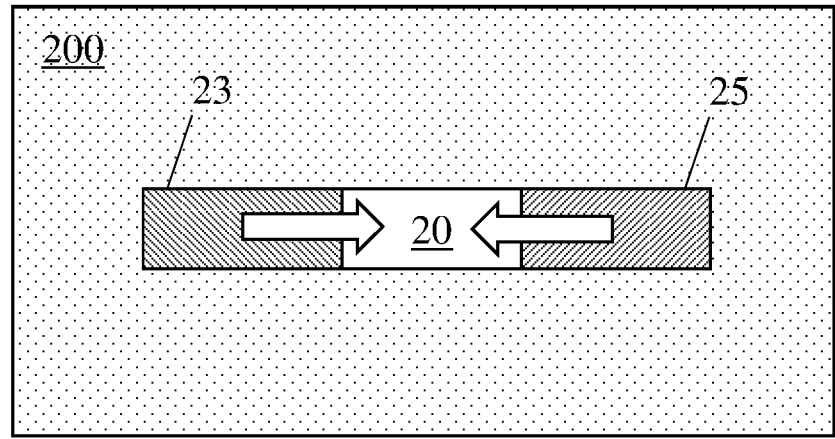
Figure 2C:
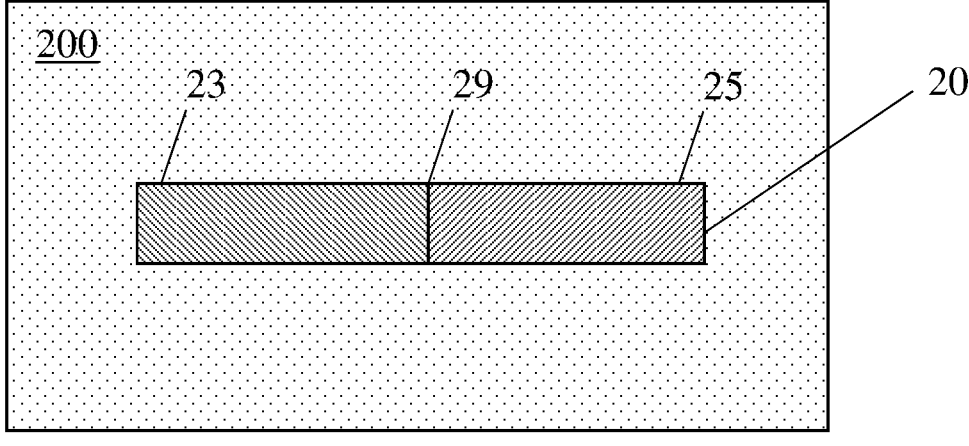

FIGS. 2A-2C show one non-limiting embodiment of a method in which two fluids flow through a channel in different directions and then meet at an interface between the fluid fronts of the fluids (e.g., the fluid/air interface of the first fluid meets with the fluid/air interface of the second fluid). In FIG. 2A, a first fluid 23 and a second fluid 25 are initially present at opposite ends of a channel 20 in a layer 200. In FIG. 2B, the two fluids have flowed towards each other along the directions indicated by the arrows, but have not yet met. In FIG. 2C, the first and second fluids are meeting at interface 29. The interface is an interface between the fluid fronts of the two fluids.

In some embodiments, one or both of the first fluid and second fluid (and/or one or both of the first portion of the fluid sample and the second portion of the fluid sample) comprise a reagent. The reagent may be configured to react with a species in the other fluid or portion of the fluid sample (e.g., a reagent therein, a reaction product of a species present in the fluid or portion of the fluid sample with a reagent, a species present in the fluid or portion of the fluid sample), or may be configured to react with a species that may be present in the fluid or portion of the fluid sample (e.g., a species the fluidic device is configured to assay, a reaction product of the species the fluidic device is configured to assay). When the fluids and/or portions of fluid samples meet, they may react to form a detectable signal. The detectable signal may be localized to the interface between the fluids and/or fluid samples, though diffusion of the reaction product may occur at or near the interface.

Figure 1C:
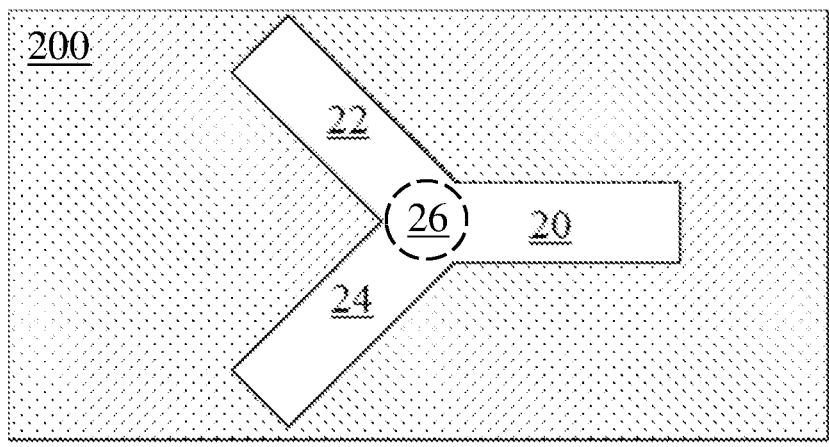
FIG. 1C shows a bottom view of a fluidic device comprising a layer comprising three channels that intersect, according to some embodiments.

In some embodiments, a fluidic device comprises a layer comprising more than one channel that intersect. For instance, the fluidic device may comprise two channels that intersect, three channels that intersect, four channels that intersect, or more channels that intersect. The channels may all intersect in a single intersection (e.g., two, three, four, or more channels may intersect in a single intersection), and/or some channels may intersect in one intersection while other channels intersect in another intersection (e.g., a first and second channel may intersect in a first intersection, and the first channel may intersect with a third channel in a second intersection). By way of example, FIG. 1C shows a bottom view of a fluidic device comprising a layer comprising three channels that intersect. The layer 200 in FIG. 1C comprises three channels (20, 22, and 24) that intersect in intersection 26.

Some embodiments comprise forming one or more interfaces between two or more fluids (and/or two or more portions of a fluid sample) at an intersection between two or more channels. The interface(s) may form between the fluid fronts of the fluids and/or portions of fluid samples. In some embodiments, multiple fluids and/or portions of fluid samples flowing in different channels flow into a single intersection, and multiple interfaces between the fluids are formed in the intersection (e.g., each fluid or portion of a fluid sample flowing into the intersection may form two interfaces, one with each of the two fluids or portions of a fluid sample it is positioned directly between). The fluids may flow into the intersection in different directions.

In some embodiments, three or more fluids may form three or more interfaces in an intersection, and the combination of interfaces may be particularly advantageous. For instance, an intersection may receive a fluid sample to be analyzed comprising an unknown concentration of a species, a fluid comprising a reagent configured to react with the species, and a fluid comprising a known concentration of the species. At the intersection, the second and third fluids will react at the interface therebetween to form a detectable signal with an intensity and width dependent on the concentration of the reagent in the second fluid and the known concentration of the species in the third fluid. Also at the intersection, the first and second fluids will react at the interface therebetween to form a detectable signal with an intensity and width dependent on the concentration of the reagent in the second fluid and the concentration of the species in the first fluid. The intensity and width of the detectable signal at the interface between the first fluid and the second fluid may be compared to the intensity and width of the detectable signal at the interface between the second fluid and the third fluid to determine whether or not the concentration of the species in the first fluid is greater than, equivalent to, or less than the known concentration of the species in the third fluid. By way of example, a detectable signal at the interface of the first and second fluids having a width and intensity greater than the width and intensity at the interface between the second and third fluids may be indicative of a higher concentration of the species in the first fluid than the third fluid. By following this procedure, a user of the fluidic device with the relevant structure may be able to quickly and easily determine whether a fluid sample includes an amount of a species above, below, or equivalent to a known concentration, such as a concentration of particular diagnostic relevance.

Figure 2D:
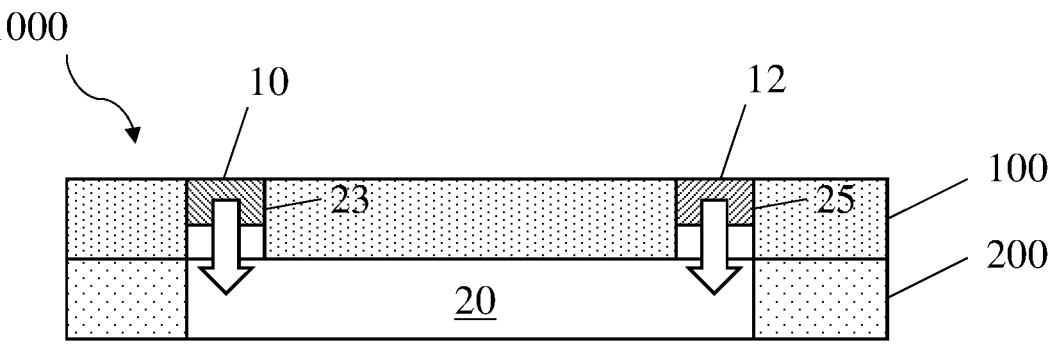
FIGS. 2D-2F show one non-limiting embodiment of a method in which two fluids flow through two disconnected regions in a layer, according to some embodiments.
Figure 2E:
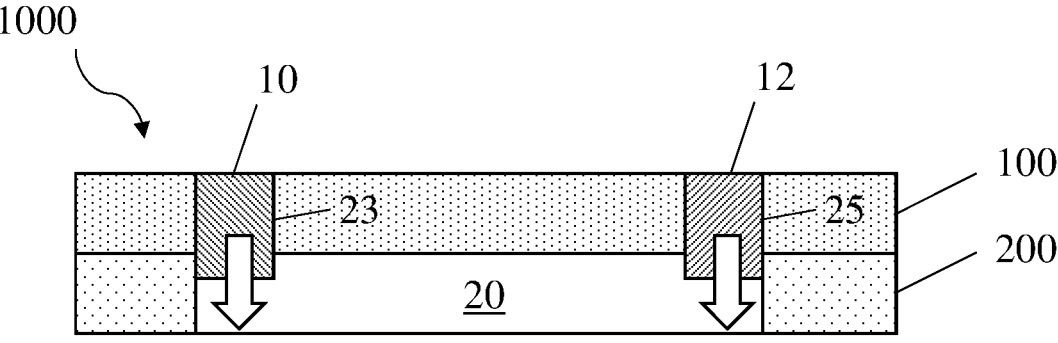
Figure 2F:
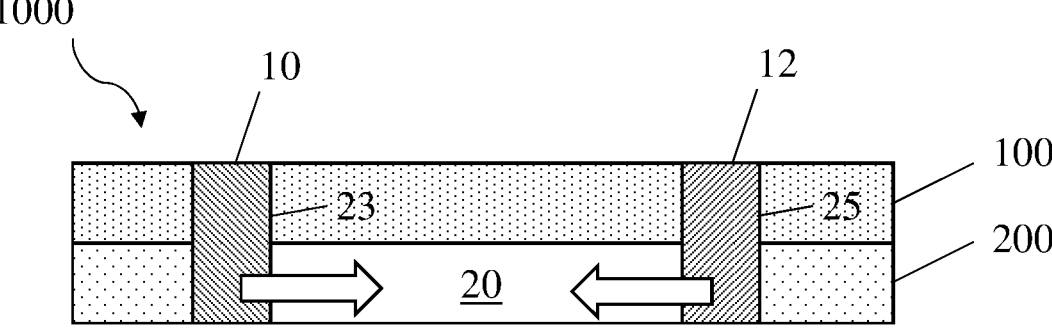

In some embodiments, fluids and/or portions of a fluid sample may flow through a first layer disposed on a second layer comprising one or more channels, prior to flowing through the channel(s) in the second layer. For example, a first fluid or a first portion of a fluid sample may flow through a first region in the first layer and into a channel in the second layer. The first fluid may then flow through all or a portion of the channel in the second layer. A second fluid (e.g., a second fluid different than the first fluid, a second fluid sample formed from a fluid sample from which the first fluid sample is also formed) and/or a second portion of the fluid sample may flow through a second region in the first layer and into all or a portion of a channel in the second layer. Referring to FIGS. 2D-2F, a first fluid 23 may flow through a first region 10 in a first layer 100 prior to flowing into a channel 20 in a second layer 200. A second fluid 25 may flow through a second region 20 in the first layer prior to flowing into the channel in the second layer. As shown illustratively in FIG. 2F, fluids 23 and 26 may flow towards each other in the direction of the arrows until the channel is filled with fluid. The two fluids may meet at an interface where a reaction may occur, as described herein. Once the channel is filled, fluid flow may cease; however, the components within the fluids may undergo a chemical and/or biological reaction or interaction at the interface, e.g., by diffusion of the sample components.

The channel in the second layer in which the second fluid flows may be the same channel through which the first fluid or first portion of a fluid sample flows (e.g., the second fluid may flow into the channel and then through it in a direction opposite to the direction the first fluid flows through it), or it may be a different channel than the channel into which the first fluid or first portion of a fluid sample flows (e.g., the second fluid may flow into a channel intersecting the channel through which the first fluid or first portion of a fluid sample flows). The first and second fluids or first and second portions of a fluid sample may flow in opposite directions through the channel(s) in the second layer, or may flow in directions in the second layer that intersect each other (e.g., the fluids or first and second portions of a fluid sample may flow at an angle to each other other than 180° along channels that intersect). In some embodiments, the first and second fluids may flow towards each other and/or may flow such that they meet at an interface.

As described herein, some embodiments comprise flowing fluids and/or portions of fluid samples through layers and/or through regions and/or channels within layers. It should be understood that, unless otherwise indicated, flowing a sample through a layer, region within a layer, and/or channel within a layer involve, in some embodiments, flowing the sample and/or portion of the sample across the thickness of the layer. In other embodiments, flowing a sample through a layer, region within a layer, and/or channel within a layer does not involve flowing the sample and/or portion of the sample across the thickness of the layer.

Figure 3A:
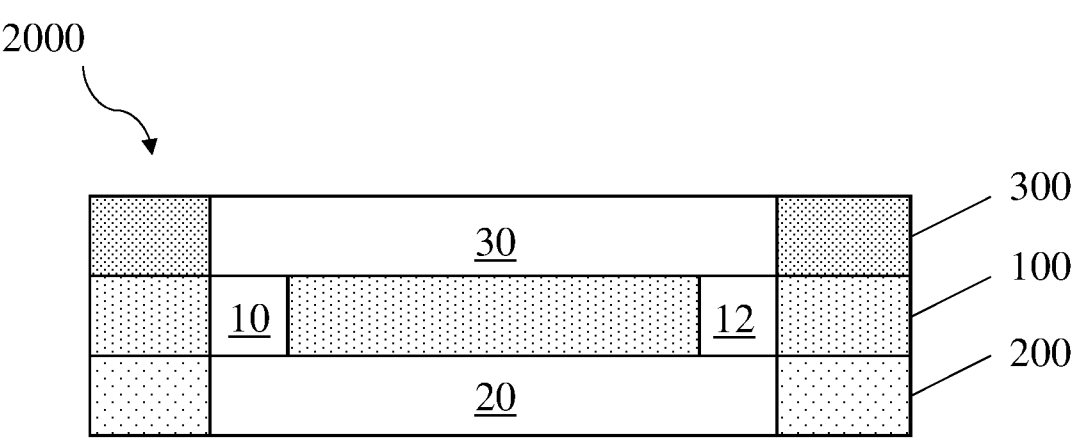
FIG. 3A shows one non-limiting example of a device in which the first layer includes two disconnected regions and the third layer comprises at least one channel in fluidic communication with both of the disconnected regions of the first layer, according to some embodiments.

In some embodiments, a fluidic device comprises the two layers shown in FIGS. 1A-1C, and further comprises a third layer disposed on the first layer. The third layer may comprise one or more channels and/or regions suitable for fluid flow. The one or more channels or regions may be in fluidic communication with one or more disconnected regions in the first layer. For instance, for a device in which the first layer includes two disconnected regions, the third layer may comprise at least one channel in fluidic communication with both of the disconnected regions of the first layer. FIG. 3A shows one non-limiting example of a device with this design. In FIG. 3A, a fluidic device 2000 comprises a first layer 100, a second layer 200, and a third layer 300. The first layer 100 comprises two disconnected regions 10 and 12. The second layer 200 comprises a channel 20. The third layer 300 comprises a channel 30. In some embodiments, the channels in the second and third layers are in fluidic communication with each other through the disconnected regions in the first layer. In some embodiments, the channels in the second and third layers are not in fluidic communication with each other other than through the disconnected regions in the first layer (and/or a subset of the disconnected regions in the first layer).

Figure 3B:
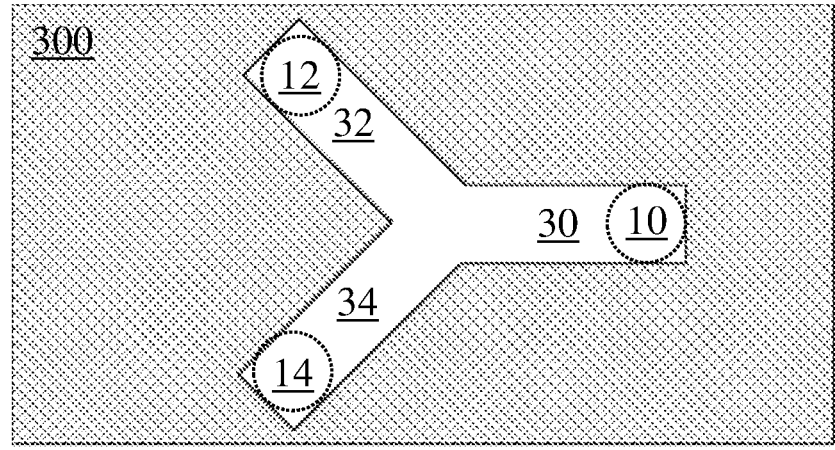
FIG. 3B shows one non-limiting embodiment of a top view of a fluidic device comprising a third layer comprising three channels, each of which is positioned on a single disconnected region in the first layer, according to some embodiments.

When a third layer comprises more than one channel, the channels therein may be positioned such that each disconnected region (e.g., in a first layer) may be positioned on (e.g., above or below) a different channel, or two or more disconnected regions may be positioned on (e.g., above or below) a single channel. FIG. 3B shows one non-limiting embodiment of a top view of a fluidic device comprising a third layer comprising three channels, each of which is positioned on (e.g., above) a single disconnected region in the first layer. In FIG. 3B, the layer 300 comprises a first channel 30, a second channel 32, and a third channel 34. The layer 100 (not shown) comprises a first disconnected region 10, a second disconnected region 12, and a third disconnected region 14. In FIG. 3B, the first disconnected region is positioned on (e.g., below) the first channel, the second disconnected region is positioned on (e.g., below) the second channel, and the third disconnected region is positioned on (e.g., below) the third channel. The disconnected regions may be positioned directly on (e.g., directly below) the channel(s), or one or more intervening layers may be positioned between the disconnected regions and the channel(s).

In some embodiments, one or more regions in a layer (e.g., one or more disconnected regions) and/or one or more portions of a channel in a layer may comprise one or more reagents. The fluidic device may be configured such that different fluids and/or different portions of a fluid sample flow through different combinations of reagents. For example, a first fluid and/or a first portion of a fluid sample may flow through a first region in a layer comprising a first set of reagents and a second fluid sample and/or a second portion of the fluid sample may flow through a second region disconnected from the first region in the layer and comprising a second set of reagents differing from the first set of reagents. In this example, the first fluid and/or first portion of the fluid sample does not flow through the second region in the layer and the second fluid sample and/or second portion of the fluid sample does not flow through the first region in the layer. As another example, the first fluid and/or first portion of a channel comprising a first set of reagents and the second fluid sample and/or second portion of the fluid sample may flow through a second portion of the channel comprising a second set of reagents differing from the first set of reagents. In this second example, the first fluid and/or first portion of the fluid sample does not flow through the second portion of the channel and the second fluid sample and/or second portion of the fluid sample does not flow through the first portion of the channel.

After flowing through different combinations of reagents, a first fluid may comprise a different combination of reagents than a second fluid, and/or a first portion of a fluid sample may then comprise a different combination of reagents than a second portion of the fluid sample. The first and second fluids (and/or first and second portions of a fluid sample) may then meet at an interface, at which reagents in the first fluid (and/or in the first portion of the fluid sample) may react with reagents in the second fluid (and/or in the second portion of the fluid sample). Other configurations are also possible.

In some embodiments, a layer adjacent to the bottommost layer comprises a region configured to facilitate detection in a portion of a layer therebeneath (e.g., a channel). For instance, this layer may be lighter in color than other portions of the layer and/or may provide a background upon which it is easier to detect the presence, absence, intensity, and/or width of a detectable signal in the portion of the layer. In some embodiments, a region configured to facilitate detection in a portion of the layer therebeneath may be a region that lacks one or more components present in other portions of the layer. By way of example, in some embodiments, a region configured to facilitate detection in a portion of the layer therebeneath may lack a barrier impermeable to fluid. As described elsewhere herein, in some embodiments, portions of a layer that are not configured to have fluid flow thereinto and/or therethrough (e.g., portions other than regions configured to receive a fluid, channels, detection regions, disconnected regions, and the like) may comprise a barrier impermeable to fluid. This barrier may, in some instances, be relatively dark and/or relatively opaque. Such features of the portions of the layer comprising the barrier impermeable to fluid may make it challenging to detect one or more features of a detectable signal (or its absence) with common detection tools (such as the eye, a camera, and the like) when serving as a background to the detectable signal. A region lacking this barrier impermeable to fluid may have other features of the portion(s) of the layer lacking the barrier impermeable to fluid, such as its color, which may facilitate detection of a detectable signal in the portion of the layer therebeneath.

Figure 3C:
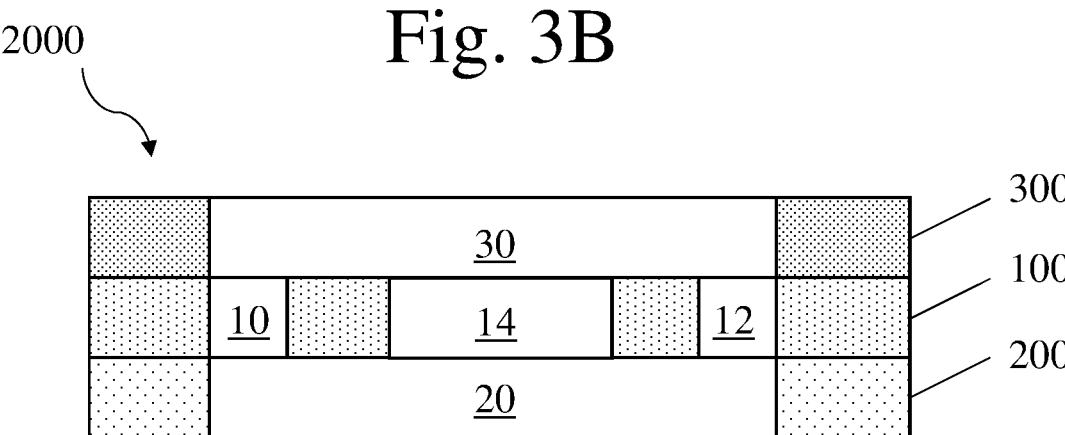
FIG. 3C shows one non-limiting example of a device in which the first layer includes two disconnected regions and a region configured to facilitate in a portion of a layer therebeneath, the second layer comprises a channel, and the third layer comprises a channel, according to some embodiments.

FIG. 3C shows one example of a layer comprising a region configured to facilitate detection in a portion of a layer therebeneath. In FIG. 3C, a fluidic device 2000 comprises a first layer 100, a second layer 200, and a third layer 300. The first layer 100 comprises two disconnected regions 10 and 12 and further comprises a region configured to facilitate detection in a portion of a layer therebeneath 14. The second layer 200 comprises a channel 20. The third layer 300 comprises a channel 30. The device shown in FIG. 3C may be particularly advantageous when a detectable signal is configured to be formed in a portion of the channel 20 positioned directly beneath the region configured to facilitate detection in a portion of a layer therebeneath 14.

As described above with respect to FIG. 1A, it should be understood that a device may comprise the layers shown in FIG. 3A, 3B, or 3C but may differ from FIG. 3A, FIGS. 3B, and/or 3C in one or more ways. For instance, one or more layers may be positioned between the first layer and the third layer (or the first and third layers may be directly adjacent as shown in FIG. 3A), one or more layers may be disposed on the third layer, and/or the second layer may be disposed on one or more layers. Additionally or alternatively, some fluidic devices may comprise disconnected regions and/or fluidic channels that differ from those shown in FIGS. 3A-3C (e.g., in one or more of the ways described above with respect to FIG. 1A). In many, but not all, embodiments, a device comprising two layers surrounding a layer comprising disconnected regions comprises an equal number of channels in the layers above and below the disconnected regions. For instance, a device may comprise first and third layers with equal numbers of channels. The design and/or arrangement of the channels in the layers on (e.g., above and below) the disconnected regions may also be similar or the same.

Some methods may comprise flowing a fluid sample through a fluidic device comprising a first layer comprising two or more regions disconnected from each other in the first layer, a second layer positioned below the first layer and comprising a channel, and a third layer disposed on the first layer and comprising a channel. In other words, some methods may comprise flowing a fluid sample through a fluidic device comprising the layers shown in FIGS. 3A-3C.

The fluid sample may flow through the channel or channels in the second layer such that portions of the fluid sample flow into the disconnected regions in the first layer. The portions of the fluid sample may flow through the disconnected regions in the second layer into the channel or channels in the third layer. As described above with respect to FIGS. 1A-1C, the portions of the fluid sample may flow through the channel or channels in the third layer to meet at an interface. The interface may be between two portions of the fluid sample flowing in different directions in a single channel (e.g., flowing in opposite directions), or may be between two or more portions of the fluid sample flowing through two or more channels into an intersection (e.g., flowing in different, possibly opposite, directions). In some embodiments, the interface may be between the fluid fronts of the portions of the fluid sample meeting at the interface. In some embodiments, a method comprises splitting a fluid sample (e.g., in one or more channels in a third layer), flowing different portions of the split fluid sample through different disconnected regions (e.g., in the first layer), and then recombining the split fluid sample (e.g., at the interface(s) between the portions of the split fluid sample).

Figure 4:
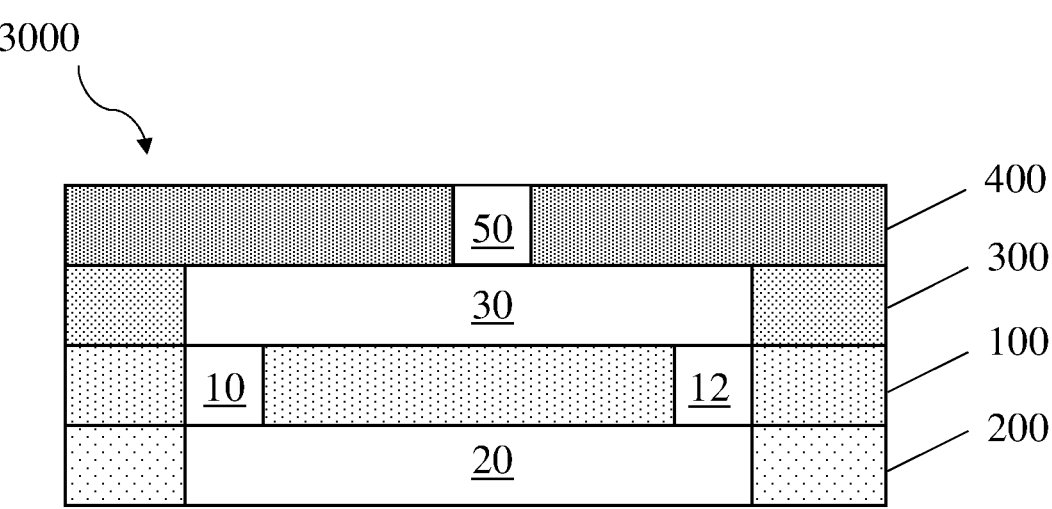
FIG. 4 shows one non-limiting embodiment of a fluidic device comprising four layers, according to some embodiments.

In some embodiments, a fluidic device comprises the layers shown in FIGS. 3A-3C, and further comprises a fourth layer disposed on the third layer shown in FIGS. 3A-3C. The fourth layer may comprise a region in fluidic communication with an environment external to the fluidic device. FIG. 4 shows one non-limiting embodiment of a fluidic device with this design. In FIG. 4, a fluidic device 3000 comprises a first layer 100, a second layer 200, a third layer 300, and a fourth layer 400. The first layer 100 comprises two disconnected regions 10 and 12. The second layer 200 comprises a channel 20. The third layer 300 comprises a channel 30. The fourth layer comprises a region 50 in fluidic communication with an environment external to the fluidic device. In some embodiments, region 50 (e.g., a sample introduction region or fluid introduction region) may be in fluidic communication with an environment external to the fluidic device is configured to receive a sample or other suitable fluid (e.g., from the environment external to the fluidic device). The sample received by the region may flow from the region into the device and then into and/or through any regions and/or channels therein.

In some embodiments, the region (e.g., a sample introduction region or fluid introduction region) in fluidic communication with an environment external to the fluidic device may be positioned centrally (e.g., with respect to the channel or channels in the layer on which the layer in which it is positioned is disposed, with respect to the layer in which it is positioned, and/or with respect to the layer on which the layer in which it is positioned is disposed). In other embodiments, the region (e.g., a sample introduction region or fluid introduction region) is not positioned centrally.

As one example of device 3000 in use, a fluid sample may be introduced into region 50, and may flow towards channel 30. There, the fluid sample may split into two sample portions: one that flows in one direction (e.g., to the left) in channel 30, and another that flows in another direction (e.g., to the right) in channel 30. The portions of the fluid sample may flow through the disconnected regions 10 and 12 in the first layer into the channel or channels in the third layer. For instance, the sample fluids may flow towards each other in channel 20 and meet at an interface. In some embodiments, the interface may be between the fluid fronts of the portions of the fluid sample meeting at the interface.

As described above with respect to FIG. 1A and FIGS. 3A-3C, it should be understood that a device may comprise the layers shown in FIG. 4 but may differ from FIG. 4 in one or more ways. For instance, one or more layers may be positioned between the third layer and the fourth layer (or the third and fourth layers may be directly adjacent as shown in FIG. 4), one or more layers may be disposed on the fourth layer, and/or the second layer may be disposed on one or more layers. Additionally or alternatively, some fluidic devices may comprise disconnected regions and/or fluidic channels that differ from those shown in FIG. 4 (e.g., in one or more of the ways described above with respect to FIG. 1A).

Figure 5:
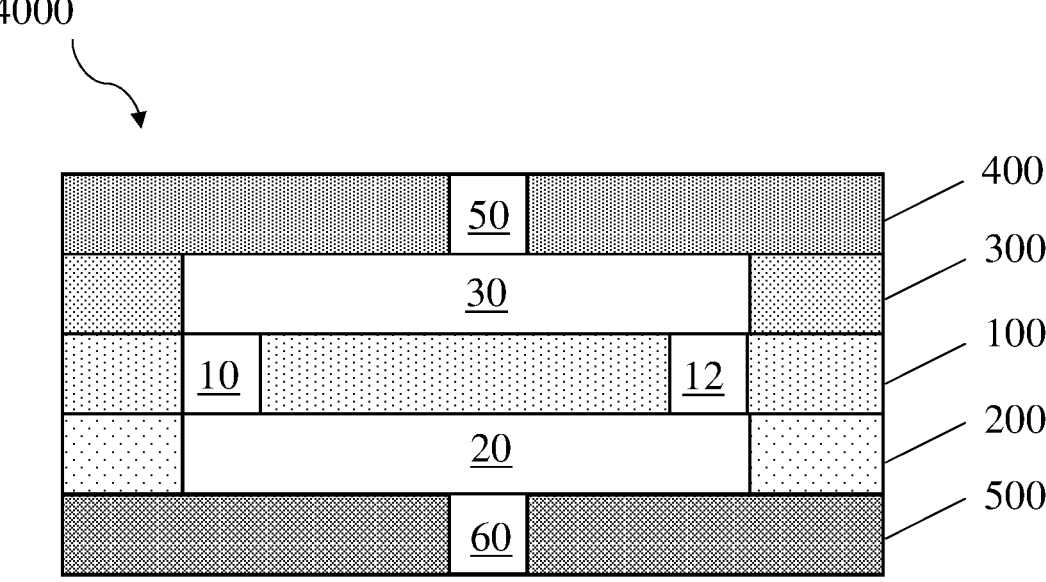
FIG. 5 shows one non-limiting embodiment of a fluidic device comprising five layers, according to some embodiments.

In some embodiments, a fluidic device comprises the layers shown in FIG. 1A, the layers shown in FIGS. 3A-3C, and/or the layers shown in FIG. 4 and further comprises a fifth layer positioned on (e.g., below) the second layer. FIG. 5 shows one non-limiting embodiment of a fluidic device with this design. In FIG. 5, the fluidic device comprises five layers, as will be described in further detail below. However, it should be understood that some fluidic devices may comprise the fifth layer shown in FIG. 4 and may lack one or more of the layers also shown in FIG. 5 (e.g., some fluidic devices may lack the third and/or fourth layers shown in FIG. 5). In FIG. 5, a fluidic device 4000 comprises a first layer 100, a second layer 200, a third layer 300, a fourth layer 400, and a fifth layer 500. The first layer 100 comprises two disconnected regions 10 and 12. The second layer 200 comprises a channel 20. The third layer 300 comprises a channel 30. The fourth layer comprises a region 50 in fluidic communication with an environment external to the fluidic device. The fifth layer comprises a detection region 60. The detection region may be configured such that an interface between one or more fluids in the second and/or fifth layers is easily detectable and/or such that a detectable signal formed at an interface between one or more fluids in the second and/or fifth layers is easily detectable. In some embodiments, the detection region is positioned directly below a channel (and/or an intersection of one or more channels) in the second layer. The detection region may be in fluidic communication with a channel (and/or an intersection of one or more channels) in the second layer.

As described above with respect to FIG. 1A, FIGS. 3A-3C, and FIG. 4, it should be understood that a device may comprise the layers shown in FIG. 5 but may differ from FIG. 5 in one or more ways. For instance, one or more layers may be positioned between the second layer and the fifth layer (or the second and fifth layers may be directly adjacent as shown in FIG. 5), one or more layers may be disposed on the fourth layer, and/or the fifth layer may be disposed on one or more layers. Additionally or alternatively, some fluidic devices may comprise disconnected regions and/or fluidic channels that differ from those shown in FIG. 5 (e.g., in one or more of the ways described above with respect to FIG. 1A).

A variety of devices comprising channels, disconnected regions, regions in fluidic communication with an environment external to the fluidic device, and sample regions are shown in FIGS. 1-5. In some embodiments, like in FIGS. 1-5, a fluidic device may comprise exclusively channels and regions that are in fluidic communication with each other. For instance, a fluidic device may comprise a single region (e.g., sample introduction region, fluid introduction region) in fluidic communication with an environment external to the fluidic device and/or a single detection region. In other embodiments, a fluidic device may comprise two or more sets of channels and regions that are in fluidic communication with each other but not in fluidic communication with other sets of channels and regions. By way of example, a fluidic device may comprise multiple regions in fluidic communication with an environment external to the fluidic device but not in fluidic communication with each other through the fluidic device and/or multiple detection regions that are not in fluidic communication with each other. Fluidic devices comprising two or more sets of channels and regions that are in fluidic communication with each other but not in fluidic communication with other sets of channels and regions may be suitable for performing analyses of multiple fluid samples. Each fluid sample may be introduced to the fluidic device through a separate region in fluidic communication with an environment external to the fluidic device, flow through a separate set of regions and channels within the fluidic device, and then flow to separate detection regions to meet at separate interfaces and form separate detectable signals. Fluidic devices suitable for performing analyses of multiple fluid samples may be configured to perform the same type of analysis on each fluid sample (e.g., the fluidic device may comprise two or more identical combinations of channels and regions and/or identical combinations of reagents) and/or may be configured to perform different types of analysis on different fluid samples (e.g., the fluidic device may comprise two or more different combinations of channels and regions and/or different combinations of reagents).

As described above, fluidic devices described herein may comprise one or more channels. The channels may be open channels (e.g., the channels may be open along two sides, or open along one side), or the channels may be enclosed. The channels may have a variety of suitable dimensions. In some embodiments, one or more channels are present in a layer, and the channel extends through the thickness of the layer. In other words, some channels may have the same thickness as the layers in which they are positioned. In some embodiments, one or more channels may have dimensions that aid in metering of a fluid sample. The channel(s) may have a volume, dimension, and/or shape that promotes flow of a desired volume of the fluid sample therein and/or therethrough.

A fluidic device may comprise a channel with a thickness or height of greater than or equal to 50 microns, greater than or equal to 75 microns, greater than or equal to 100 microns, greater than or equal to 125 microns, greater than or equal to 150 microns, greater than or equal to 200 microns, greater than or equal to 250 microns, greater than or equal to 300 microns, greater than or equal to 400 microns, greater than or equal to 500 microns, greater than or equal to 750 microns, or greater than or equal to 1 mm. The fluidic device may comprise a channel with a thickness or height of less than or equal to 2 mm, less than or equal to 1 mm, less than or equal to 750 microns, less than or equal to 500 microns, less than or equal to 400 microns, less than or equal to 300 microns, less than or equal to 250 microns, less than or equal to 200 microns, less than or equal to 150 microns, less than or equal to 125 microns, less than or equal to 100 microns, or less than or equal to 75 microns. Combinations of the above-referenced ranges are also possible (e.g., greater than or equal to 50 microns and less than or equal to 2 mm, greater than or equal to 50 microns and less than or equal to 500 microns, or greater than or equal to 50 microns and less than or equal to 100 microns). Other ranges are also possible.

Channels in fluidic devices may have a variety of suitable widths. In some embodiments, a fluidic device comprises a channel with a width of greater than or equal to 500 microns, greater than or equal to 750 microns, greater than or equal to 1 mm, greater than or equal to 1.5 mm, greater than or equal to 2 mm, greater than or equal to 2.5 mm, greater than or equal to 3 mm, greater than or equal to 3.5 mm, greater than or equal to 4 mm, or greater than or equal to 4.5 mm. The fluidic device may comprise a channel with a width of less than or equal to 5 mm, less than or equal to 4.5 mm, less than or equal to 4 mm, less than or equal to 3.5 mm, less than or equal to 3 mm, less than or equal to 2.5 mm, less than or equal to 2 mm, less than or equal to 1.5 mm, less than or equal to 1 mm, or less than or equal to 750 microns. Combinations of the above-referenced ranges are also possible (e.g., greater than or equal to 500 microns and less than or equal to 5 mm, or greater than or equal to 2 mm and less than or equal to 5 mm). Other ranges are also possible.

Channels in fluidic devices may have a variety of suitable aspect ratios (i.e., ratios of the channel length to the channel width). In some embodiments, a fluidic device comprises a channel with an aspect ratio of greater than or equal to 3:1, greater than or equal to 5:1, greater than or equal to 7:1, greater than or equal to 10:1, greater than or equal to 20:1, greater than or equal to 50:1, or greater than or equal to 70:1. The fluidic device may comprise a channel with an aspect ratio of less than or equal to 100:1, less than or equal to 70:1, less than or equal to 50:1, less than or equal to 20:1, less than or equal to 10:1, less than or equal to 7:1, or less than or equal to 5:1. Combinations of the above-referenced ranges are also possible (e.g., greater than or equal to 3:1 and less than or equal to 100:1). Other ranges are also possible.

Channels in fluidic devices described herein may have a variety of suitable volumes. In some embodiments, it may be desirable for a channel to have a volume such that it is configured to receive a desirable amount of a fluid sample. For instance, a channel may have a volume such that a sample region therein becomes saturated with an appropriate amount of a fluidic sample for one or more analyses after exposure to the fluid sample. In some embodiments, a channel may have a relatively low volume, so that the channel and/or one or more sample regions therein may be saturated after the channel has received a relatively low volume of the fluidic sample. This may be desirable for fluid samples that are expensive and/or difficult to procure large amounts of.

In some embodiments, a fluidic device comprises a channel with a volume of greater than or equal to 1 μL, greater than or equal to 2 μL, greater than or equal to 5 μL, greater than or equal to 10 μL, greater than or equal to 15 μL, greater than or equal to 20 μL, greater than or equal to 30 μL, greater than or equal to 40 μL, greater than or equal to 50 μL, greater than or equal to 75 μL, greater than or equal to 100 μL, greater than or equal to 150 μL, greater than or equal to 200 μL, greater than or equal to 300 μL, greater than or equal to 400 μL, greater than or equal to 500 μL, or greater than or equal to 750 μL. The fluidic device may comprise a channel with a volume of less than or equal to 1 mL, less than or equal to 750 μL, less than or equal to 500 μL, less than or equal to 400 μL, less than or equal to 300 μL, less than or equal to 200 μL, less than or equal to 150 μL, less than or equal to 100 μL, less than or equal to 75 μL, less than or equal to 50 μL, less than or equal to 40 μL, less than or equal to 30 μL, less than or equal to 20 μL, less than or equal to 15 μL, less than or equal to 10 μL, less than or equal to 5 μL, or less than or equal to 2 μL. Combinations of the above-referenced ranges are also possible (e.g., greater than or equal to 1 μL and less than or equal to 50 μL). Other ranges are also possible. In some embodiments, a channel comprises a sample region with a volume in one or more of the ranges described above (e.g., a channel may comprise a sample region with a volume of greater than or equal to 1 μL and less than or equal to 1 mL, greater than or equal to 1 μL and less than or equal to 50 μL, or greater than or equal to 100 μL and less than or equal to 300 μL).

In some embodiments, a fluidic device comprises two or more channels that have relatively similar volumes. The channels with the relatively similar volumes may be in the same layer (e.g., two or more channels that extend from a region in fluidic communication with an environment external to the microfluidic device and/or two or more channels through which different portions of a fluidic sample may flow may have relatively similar volumes). Relatively similar volumes of a fluidic sample may flow into and/or through channels with relatively similar volumes. In some embodiments, two channels may have volumes that differ by no more than 500%, no more than 400%, no more than 300%, no more than 200%, no more than 100%, no more than 50%, no more than 25%, no more than 10%, no more than 5%, no more than 2%, or no more than 1%.

In some embodiments, a fluidic device may comprise two or more channels that have volumes differing outside of the ranges described above (e.g., channels in different layers of the fluidic device). It should be understood that a fluidic device may comprise two or more channels that have relatively similar volumes (e.g., volumes that differ by an amount in one or more of the ranges described above) and may comprise two or more channels that have relatively different volumes (e.g., volumes that differ by an amount outside of one or more of the ranges described above.

As described above, fluidic devices described herein may comprise one or more layers. In some embodiments, one or more of the layers of the fluidic device comprises a porous material (e.g., one or more layers comprising one or more channels, one or more disconnected regions, one or more detection regions, and/or one or more regions in fluidic communication with an environment external to the fluidic device). The porous material may be absorbent, or may not be absorbent. A porous, absorbent material may, upon exposure to a fluid, wick the fluid into the layer and/or wick the fluid through the layer. When layers comprising channels comprise a porous, absorbent material, the porous, absorbent material may wick the fluid into the channels therein and/or through the channels therein. In some embodiments, a fluid may flow into and/or through a porous, absorbent material due to capillarity (capillary action) or by wicking. In some embodiments, a porous, absorbent material will, upon exposure to a fluid (e.g., a fluid sample of interest, a fluid sample for which it is absorbent), transport the fluid into the interior of the porous, absorbent material (i.e., the fluid sample may penetrate into the interior of the material in which the pores are positioned, such as into the interior of fibers making up a porous, absorbent material that comprises fibers). In some embodiments, a porous, absorbent material will, upon exposure to a fluid, experience an increase in mass due to the fluid absorbed therein. It should be understood that some layers comprising porous absorbent materials may have one or more of the properties described above with respect to porous, absorbent materials.

In some embodiments, a fluidic device comprises a porous, absorbent material that is hydrophilic and/or may comprise a layer that is hydrophilic (e.g., a layer comprising a hydrophilic porous, absorbent material). The hydrophilic material or layer may have a water contact angle of less than or equal to 90°, less than or equal to 85°, less than or equal to 80°, less than or equal to 75°, less than or equal to 70°, less than or equal to 65°, less than or equal to 60°, less than or equal to 55°, less than or equal to 50°, less than or equal to 45°, less than or equal to 40°, less than or equal to 35°, less than or equal to 30°, less than or equal to 25°, less than or equal to 20°, less than or equal to 15°, less than or equal to 10°, or less than or equal to 5°. The hydrophilic material or layer may have a water contact angle of greater than or equal to 0°, greater than or equal to 5°, greater than or equal to 10°, greater than or equal to 15°, greater than or equal to 20°, greater than or equal to 25°, greater than or equal to 30°, greater than or equal to 35°, greater than or equal to 40°, greater than or equal to 45°, greater than or equal to 50°, greater than or equal to 55°, greater than or equal to 60°, greater than or equal to 65°, greater than or equal to 70°, greater than or equal to 75°, greater than or equal to 80°, or greater than or equal to 85°. Combinations of the above-referenced ranges are also possible (e.g., less than or equal to 90° and greater than or equal to 0°). Other ranges are also possible. The water contact angle of a hydrophilic material or layer may be measured using ASTM D5946-04, which comprises positioning a water droplet on a planar solid surface of the hydrophilic material or layer. The water contact angle is the angle between the planar solid surface of the hydrophilic material or layer and the tangent line drawn to the water droplet surface at the three-phase point. A contact angle meter or goniometer can be used for this determination. In some embodiments, the hydrophilicity of the hydrophilic material or layer may be such that a water droplet placed on the surface completely wets the surface (e.g., the water droplet is completely absorbed into the material making the water contact angle 0°). In some embodiments, a device may comprise a porous, absorbent material that is hydrophobic and/or may comprise a layer that is hydrophobic. The hydrophobic material or layer may have a water contact angle outside the ranges described above.

In some embodiments, a porous, absorbent material is a cellulose-based material. The cellulose-based material may comprise cellulose derived from wood (e.g., it may be a wood-based material), cellulose derived from cotton (e.g., it may be a cotton-based material), and/or nitrocellulose.

In some embodiments, a porous, absorbent material comprises a synthetic material and/or a glass. Non-limiting examples of suitable synthetic materials include poly(ether sulfone), polyesters, and nylons.

Porous materials described herein (e.g., porous, absorbent materials described herein) may have a variety of designs. In some embodiments, a fluidic device comprises a porous material that is a fibrous material (e.g., a fibrous material comprising fibers formed from a cellulose-based material). The fibrous material may be a non-woven material, or may be a woven material. The fibers may have a variety of suitable diameters and distributions of diameters, and, if woven, may be woven in a variety of suitable weaves. In some embodiments, the non-woven material is a paper, such as a cellulose-based paper. A wide variety of commercially available cellulose-based papers may be employed, such as those manufactured by Whatman, those manufactured by Ahlstrom, and/or those manufactured by Munktell.

Fibrous materials may comprise fibers having any suitable average fiber diameter. The average fiber diameter of the fibers may be greater than or equal to 0.1 micron, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 15 microns, greater than or equal to 20 microns, greater than or equal to 25 microns, greater than or equal to 30 microns, greater than or equal to 40 microns, greater than or equal to 50 microns, greater than or equal to 60 microns, or greater than or equal to 70 microns. The average fiber diameter of the fibers may be less than or equal to 75 microns, less than or equal to 70 microns, less than or equal to 60 microns, less than or equal to 50 microns, less than or equal to 40 microns, less than or equal to 30 microns, less than or equal to 25 microns, less than or equal to 20 microns, less than or equal to 15 microns, less than or equal to 10 microns, less than or equal to 5 microns, less than or equal to 2 microns, less than or equal to 1 micron, less than or equal to 0.5 microns, or less than or equal to 0.2 microns. Combinations of the above-referenced ranges are also possible (e.g., greater than or equal to 0.1 micron and less than or equal to 75 microns). Other ranges are also possible. The average fiber diameter may be determined using electron microscopy.

Porous materials (e.g., porous, absorbent materials) and layers comprising porous materials (e.g., layers comprising porous, absorbent materials) described herein may have a variety of suitable porosities. The porosity of a porous and/or a layer comprising a porous may be greater than or equal to 1 vol %, greater than or equal to 2 vol %, greater than or equal to 5 vol %, greater than or equal to 10 vol %, greater than or equal to 20 vol %, greater than or equal to 50 vol %, greater than or equal to 55 vol %, greater than or equal to 60 vol %, greater than or equal to 65 vol %, greater than or equal to 70 vol %, or greater than or equal to 75 vol %, or greater than or equal to 80 vol %. The porosity of a porous material and/or a layer comprising a porous material may be less than or equal to 85 vol %, less than or equal to 80 vol %, less than or equal to 75 vol %, less than or equal to 70 vol %, less than or equal to 65 vol %, less than or equal to 60 vol %, less than or equal to 55 vol %, less than or equal to 50 vol %, less than or equal to 20 vol %, less than or equal to 10 vol %, less than or equal to 5 vol %, or less than or equal to 2 vol %. Combinations of the above-referenced ranges are also possible (e.g., greater than or equal to 1 vol % and less than or equal to 85 vol %, greater than or equal to 1 vol % and less than or equal to 80 vol %, or greater than or equal to 50 vol % and less than or equal to 80 vol %). Other ranges are also possible. The porosity of a material or a layer may be determined by mercury intrusion porosimetry.

Porous materials (e.g., porous, absorbent materials) and layers comprising porous materials (e.g., layers comprising porous, absorbent materials) described herein may comprise pores with a variety of suitable sizes. The average pore size of a porous material and/or a layer comprising a porous material may be greater than or equal to 0.1 micron, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 15 microns, greater than or equal to 20 microns, greater than or equal to 25 microns, greater than or equal to 30 microns, greater than or equal to 35 microns, greater than or equal to 40 microns, greater than or equal to 50 microns, greater than or equal to 75 microns, greater than or equal to 100 microns, or greater than or equal to 125 microns. The average pore size of a porous material and/or a layer comprising a porous material may be less than or equal to 150 microns, less than or equal to 125 microns, less than or equal to 100 microns, less than or equal to 75 microns, less than or equal to 50 microns, less than or equal to 40 microns, less than or equal to 35 microns, less than or equal to 30 microns, less than or equal to 25 microns, less than or equal to 20 microns, less than or equal to 15 microns, less than or equal to 10 microns, less than or equal to 5 microns, less than or equal to 2 microns, less than or equal to 1 micron, less than or equal to 0.5 microns, or less than or equal to 0.2 microns. Combinations of the above-referenced ranges are also possible (e.g., greater than or equal to 0.1 micron and less than or equal to 150 microns, or greater than or equal to 2 microns and less than or equal to 40 microns). Other ranges are also possible. In some embodiments, it may be advantageous for a layer in which a signal is configured to form to have a relatively low average pore size (e.g., less than or equal to 15 microns), as it is believed that relatively low average pore sizes retard diffusion of species in the layer. The average pore size of a porous material or a layer comprising a porous material may be determined by mercury intrusion porosimetry.

As described above, layers comprising porous, absorbent materials may also comprise one or more regions and/or channels. For instance, layers comprising porous, absorbent materials may also comprise a central region in fluidic communication with an environment external to a fluidic device (e.g., a region configured to receive a fluid sample from the environment external to the fluidic device), one or more channels, and/or one or more sample regions. In some embodiments, the central region, the one or more channels, and/or the one or more sample regions may be positioned in the porous, absorbent material. Regions and/or channels may be formed in a layer and/or material (e.g., a layer comprising a porous, absorbent material and/or a porous, absorbent material) by a variety of suitable methods. By way of example, a barrier impermeable to a fluid may be infiltrated into portions of the layer and/or material to define channels and/or regions therein. This may be accomplished by, e.g., printing (e.g., wax printing, 3D-printing) and/or pattern transfer methods (e.g., by use of photoresists and/or UV-curable materials). The fluid to which the barrier is impermeable (e.g., a fluid, one or more components of a fluid sample) may, upon entering a channel and/or region defined by an impermeable barrier, be confined to portions of the layer and/or material to which it can flow through the layer and/or material without crossing the impermeable barrier (e.g., channels and/or regions in fluidic communication with the channel and/or region defined by the impermeable barrier).

Barriers impermeable to a variety of fluids may be employed. In some embodiments, the fluid to which a barrier is impermeable is an aqueous fluid, such as a fluid of biological origin. Non-limiting examples of fluids of biological origin include blood (e.g., whole blood) and fluids derived from blood (e.g., plasma), cerebrospinal fluid, tissue biopsies, and milk. The barrier impermeable to a fluid may comprise a variety of suitable materials, non-limiting examples of which include waxes, polymers, and hydrophobic materials (e.g., hydrophobic waxes, hydrophobic polymers, other hydrophobic materials).

In some embodiments, a fluidic device comprises a cover layer. Advantageously, the cover layer may enclose and/or protect the fluidic device in which it is positioned. It may be impermeable to one or more fluids to be introduced into the fluidic device, may be impermeable to one or more components of an environment external to the fluidic device, may strengthen the fluidic device, and/or may decrease the tendency of the fluidic device to be damaged during handling.

A fluidic device may comprise a cover layer that is the uppermost layer and/or a cover layer that is the lowermost layer. The cover layer may further comprise one or more openings, which may be in fluidic communication with one or more features of a layer to which it is adjacent. For instance, an uppermost cover layer may comprise one or more openings in fluidic communication with a central region and/or a channel of a layer therebeneath. In some embodiments, a cover layer lacks openings and prevents fluidic communication between a layer to which it is adjacent an environment external to the fluidic device through the cover layer. For instance, a lowermost cover layer may seal the bottom of the fluidic device from direct fluidic communication with an environment beneath the fluidic device.

The cover layers described herein typically comprise materials that are relatively impermeable to a variety of fluids (e.g., aqueous fluids), relatively impermeable to a variety of gases (e.g., gases in the ambient environment), and/or relatively scuff and/or abrasion resistant. In some embodiments, a fluidic device comprises a cover layer that is a laminating sheet (such as a Fellowes laminating sheet) and/or an adhesive film. When laminating sheets and/or adhesive films are employed, the fluidic device may be assembled by laminating the other layers thereof (e.g., layers comprising channels, layers comprising central regions, layers comprising sample regions, filtration layers, layers configured to distribute fluid) in between two laminating sheets and/or adhesive films.

The fluidic devices described herein may be employed to perform a wide variety of suitable analyses on fluid samples. The fluidic device may comprise one set of reagents stored together, and/or may comprise two or more sets of reagents stored separately. In some embodiments, reagents that are stored separately may be reagents that are incompatible with each other (e.g., reagents that would react with each other upon exposure to each other) and/or reagents that, if simultaneously exposed to a fluid sample comprising a species reactive with one of the reagents, would react to form a detectable signal that it is desirable to localize to a specific portion of the fluidic device (e.g., an interface between fluids and/or portions of a fluid sample, a detectable signal that it is desirable to localize to a detection region). Reagents may be stored in a single layer (e.g., in one or more disconnected regions in the layer, in one or more portions of a channel in the layer) and/or may be stored in multiple layers (e.g., one set of reagents may be stored in a region or channel in a first layer, and another set of reagents may be stored in a region or channel in a second layer). In some embodiments, each fluid and/or portion of a fluid sample flowing through the fluidic device do not include a sufficient combination of reagents to form the final detectable signal prior to formation of an interface therebetween, but the interface formed therebetween may include a sufficient combination of reagents to form the final detectable signal. In other words, a combination of reagents sufficient to form the final detectable signal may be isolated from each other prior to combination at an interface between two or more fluids and/or portions of a fluid sample.

Reagents stored in a fluidic device (e.g., in a disconnected region, in a channel) may be stored therein in a variety of ways. Non-limiting examples of ways that reagents may be stored in the fluidic device include being adsorbed onto a material present in the fluidic device (e.g., fibers in a fibrous region or channel, a wall of a region or channel), absorbed into a material present in the fluidic device (e.g., fibers in a fibrous region or channel, a wall of a region or channel), and/or in a gel or solid material present in the fluidic device (e.g., in a region or channel). In some embodiments, the reagents may be deposited onto one or more fibers in the fluidic device (e.g., one or more fibers in a fibrous region or channel). In some embodiments, the reagents may be stored in the fluidic device as solids. The solids may be present in a matrix, such as a matrix comprising a protein (e.g., bovine serum albumin) and/or a sugar (e.g., sucralose, trehalose). In some embodiments, one or more reagents stored in a fluidic device (e.g., as solids) may be reconstituted by and/or dissolved in a fluid and/or a portion of a fluid sample flowing therethrough. For example, a fluid and/or a portion of a fluidic sample may flow through a disconnected region comprising one or more reagents, and at least a portion of the one or more reagents may dissolve in the fluid and/or the portion of the fluidic sample as it flows therethrough.

Below, examples of specific combinations of reagents, reactions, and assays are provided. It should be understood that combinations of reagents, reactions, and assays other than those described below may be employed. It should also be understood that subsets of the reagent combinations described below may be employed in some fluidic devices, the reagents may be apportioned differently between channels or regions of the fluidic device, additional reagents may be present in fluidic devices, and the like.

In some embodiments, a fluidic device described herein may be configured to perform an assay for a small molecule. The assay for the small molecule may be an enzymatic assay. A fluidic device configured to perform an enzymatic assay for a small molecule may comprise a first region or channel (or portion of a region or channel) comprising the enzyme and a second region or channel (or portion of a region or channel) comprising a co-substrate and/or co-reactant. In the case of an enzymatic assay for glucose, the enzyme is glucose oxidase and the co-reactants are horse-radish peroxidase and potassium iodide.

As another example of an assay for a small molecule, a fluidic device described herein may be configured to perform an assay for lactate. In this embodiment, a fluidic device may comprise a first region or channel (or portion of a region or channel) comprising 3-(4,5-dimethylthiazol-2-yl)-2,5-diphenyltetrazolium bromide, 1-methoxy-5-methylphenazinium methylsulfate, and TRIS buffer. The fluidic device may further comprise a second region or channel (or portion of a region or channel) comprising lactate dehydrogenase, β-nicotinamide adenine dinucleotide, and hydrazine buffer.

In some embodiments, a fluidic device described herein may be configured to perform an assay for an enzyme. The assay for the enzyme may be an enzymatic assay. A fluidic device configured to perform an enzymatic assay for an enzyme may comprise a first region or channel (or portion of a region or channel) comprising a first co-substrate and/or a co-reactant and a second region or channel (or portion of a region or channel) comprising a second co-substrate and/or co-reactant. For instance, in the case of an assay for acetyl-cholinesterase, a fluidic device may comprise a first region or channel (or portion of a region or channel) comprising acetylthiocholine and a second region or channel (or portion of a region or channel) comprising Ellman's reagent.

In some embodiments, a fluidic device described herein may be configured to perform an assay for a metal ion. The assay for the enzyme may be an assay that provides a detectable signal from a chelator of the metal ion and/or provides a detectable signal from an indicator for the metal ion. A fluidic device configured to perform an assay for a metal ion may comprise a first region or channel (or portion of a region or channel) comprising an oxidizing agent or a reducing agent and a second region or channel (or portion of a region or channel) comprising a chelator and/or an indicator for the oxidized or reduced metal ion. For instance, in the case of an assay for iron(III), a fluidic device may comprise a first region or channel (or a portion of a region or channel) comprising hydroxylamine (a reducing agent for iron(III) that reduces it to iron(II)) and a second region or channel (or portion of a region or channel) comprising ferrozine (a colorimetric chelator for iron(II)).

In some embodiments, a fluidic device described herein may be configured to perform an assay for a nucleic acid. The assay for the nucleic acid may be an assay that provides a detectable signal from the nucleic acid after hybridization. A fluidic device configured to perform an assay for a nucleic acid may comprise a first region or channel (or portion of a region or channel) comprising a capture oligo and a second region or channel (or portion of a region or channel) comprising a detector oligo and/or a hybridization indicator.

In some embodiments, a fluidic device described herein may be configured to perform an assay for an antigen. The assay for the antigen may be an assay that provides a detectable signal from an immunocomplex comprising the antigen. A fluidic device configured to perform an assay for an antigen may comprise a first region or channel (or portion of a region or channel) comprising a capture antibody and a second region or channel (or portion of a region or channel) comprising a secondary antibody and/or a complexation indicator.

The fluidic devices described herein may be suitable for performing analyses on a wide variety of fluid samples. Some methods may comprise flowing a single fluid sample to be analyzed through the fluidic device. The single fluidic sample may be split into two or more portions that pass through different portions of the fluidic device and then meet to form an interface at which a detectable signal is formed. The different portions of the fluidic sample may dissolve different reagents (e.g., reagents positioned in different disconnected regions in a layer), and, when they meet, reactions between these different reagents may occur at the interface between the portions of the fluidic sample to form a detectable signal.

Some methods may comprise flowing a fluid sample to be analyzed through the fluidic device (e.g., through one or more disconnected regions in a layer therein, through a channel therein, and/or into a detection region therein) and also flowing a second fluid not to be analyzed through the fluidic device (e.g., through one or more disconnected regions in a layer therein, through a channel therein, and/or into a detection region therein). The second fluid may be a fluid comprising one or more reagents and/or which may be employed to dissolve one or more reagents in the fluidic device. The first fluid sample may, after optionally solubilizing one or more reagents in the fluidic device, meet the second fluid at an interface in the fluidic device. The first fluid sample and the second fluid may meet at an interface, and a reaction between a reagent in the first fluid sample (e.g., a reagent initially present in the first fluid sample, a reagent originating from a portion of the fluidic device that the first sample flowed through) may react with a reagent in the second fluid (e.g., a reagent initially present in the second fluid, a reagent originating from a portion of the fluidic device that the second fluid flowed through) to produce a detectable signal.

Non-limiting examples of fluid samples that may be analyzed in the fluidic devices described herein include fluids of biological origin, such as blood (e.g., whole blood) and fluids derived from blood (e.g., plasma), cerebrospinal fluid, tissue biopsies, and milk.

Non-limiting examples of fluids that may be flowed through the fluidic device in addition to a fluid sample to be analyzed by the device (e.g., as second fluids) include aqueous fluids, such as buffers and/or water comprising a variety of dissolved species. The dissolved species may include non-buffering salts, reagents, indicators, particles, surfactants, polymers, and others.

As described elsewhere herein, some embodiments relate to fluidic devices comprising a layer comprising a detection region. The detection region may be positioned in an external or outer layer of the fluidic device (e.g., in a bottom layer) and/or a layer directly adjacent to a cover layer (e.g., directly adjacent to a bottom cover layer). In some embodiments, one or more fluids, portions of a fluid sample, and/or interfaces between fluids and/or portions of fluid samples may flow into the detection region. The detection region may comprise a porous material as described elsewhere herein, which may facilitate flow into the detection region. In some such embodiments, the detection region may comprise one or more reagents (e.g., one or more labels). In some embodiments, fluids, portions of a fluid sample, and/or interfaces between fluids and/or portions of fluid samples do not flow into the detection region. The detection region may comprise, in some embodiments, a transparent, fluid-impermeable material. The portion of the layer disposed on the detection region comprising the interface(s) at which detectable signal(s) are formed may be viewable through the material. The material may be porous and/or permeable to some fluids (e.g., air) and impermeable to others (e.g., water, aqueous fluids). In some embodiments, the material may comprise one or more reagents and/or one or more solvents, and may be configured to participate in a reaction with a fluid and/or portion of a fluid sample. In some embodiments, some or all of the portions of the layer comprising the detection region other than the detection region are opaque. These portions of the layer comprising the detection region may also be impermeable to fluids, portions of a fluid sample, and/or interfaces between fluids and/or portions of fluid samples. For instance, these portions of the detection region may comprise an opaque wax.

Detection may be performed in a variety of ways. In some embodiments, the detection may be performed optically and/or visually (i.e., the detectable signal may be detected optically and/or visually). The optical signal may be a colorimetric signal, a signal generated by chemiluminescence, and/or a signal generated by fluorescence.

In some embodiments, the detection may be performed electrochemically (i.e., the detectable signal may be detected electrochemically).

As described above, a detectable signal may form at an interface between two fluids and/or portions of a fluid sample. When the fluidic device is viewed from the top and/or the bottom, the detectable signal may appear to be a line. The line may have a length on the order of the width of the channel in which it forms or the width of the intersection in which it forms. The line may have a width of greater than or equal to 1 micron, greater than or equal to 2 microns, greater than or equal to 5 microns, greater than or equal to 10 microns, greater than or equal to 20 microns, greater than or equal to 50 microns, greater than or equal to 100 microns, greater than or equal to 200 microns, greater than or equal to 500 microns, greater than or equal to 1 mm, greater than or equal to 2 mm, or greater than or equal to 5 mm. The line may have a width of less than or equal to 10 mm, less than or equal to 5 mm, less than or equal to 2 mm, less than or equal to 1 mm, less than or equal to 500 microns, less than or equal to 200 microns, less than or equal to 100 microns, less than or equal to 50 microns, less than or equal to 20 microns, less than or equal to 10 microns, less than or equal to 5 microns, or less than or equal to 2 microns. Combinations of the above-referenced ranges are also possible (e.g., greater than or equal to 1 micron and less than or equal to 10 mm). Other ranges are also possible. As used herein, the width of the line is the average of the spatial extent of the line perpendicular to its length averaged over the entirety of the line.

When a detectable signal forms that appears to be a line forms, the line may have a width in one or more of the ranges described above for a relatively long time. The line may have a width in one or more of the ranges described above for greater than or equal to 10 seconds, greater than or equal to 20 seconds, greater than or equal to 30 seconds, greater than or equal to 45 seconds, greater than or equal to 1 minute, greater than or equal to 2 minutes, greater than or equal to 5 minutes, greater than or equal to 7 minutes, greater than or equal to 10 minutes, greater than or equal to 12 minutes, greater than or equal to 15 minutes, greater than or equal to 17 minutes, greater than or equal to 20 minutes, greater than or equal to 22 minutes, greater than or equal to 25 minutes, or greater than or equal to 27 minutes. The line may have a width in one or more of the ranges described above for less than or equal to 30 minutes, less than or equal to 27 minutes, less than or equal to 25 minutes, less than or equal to 22 minutes, less than or equal to 20 minutes, less than or equal to 17 minutes, less than or equal to 15 minutes, less than or equal to 12 minutes, less than or equal to 10 minutes, less than or equal to 7 minutes, less than or equal to 5 minutes, less than or equal to 2 minutes, less than or equal to 1 minute, less than or equal to 45 seconds, less than or equal to 30 seconds, or less than or equal to 10 seconds. Combinations of the above-referenced ranges are also possible (e.g., greater than or equal to 10 seconds and less than or equal to 30 minutes). Other ranges are also possible. The line may form instantaneously after addition of the fluid(s) to the fluidic device, or may form over a time period in one or more of the ranges described above.

In some embodiments, one or more portions of a channel or region may be functionalized to provide one or more benefits to the fluidic device. For instance, one or more portions of a channel or region may be functionalized to reduce diffusion of one or more species in that portion of the channel or region and/or out of that portion of the channel or region. By way of example, a portion of a channel or region at which an interface between two or more fluids and/or two or more portions of a fluid sample forms may be functionalized to reduce diffusion of a species giving rise to a detectable signal forming at that interface. The portion of the channel or region may be configured to reduce diffusion generally (e.g., diffusion of any species present there), or may be configured to reduce diffusion of one or more species (e.g., a species giving rise to a detectable signal) while not affecting diffusion of other species (e.g., one or more fluids and/or one or more portions of fluid samples). The functionalization may be functionalization that provides a chemical barrier to diffusion of the relevant species and/or may be functionalization that provides a physical barrier to diffusion of the relevant species. The functionalization may be chemical functionalization (e.g., functionalization that comprises changing the surface chemistry of the portion of the channel or region) and/or may be physical functionalization (e.g., functionalization that comprises adding one or more species to the portion of the channel or region that change the amount of open volume in the portion of the channel or region). Diffusion may be reduced due to electrostatic interactions, due to partitioning effects, and/or due to chromatographic effects.

Non-limiting examples of suitable types of chemical functionalization include chemically attaching one or more molecules to the portion of the channel or region and covalently cross-linking the portion of the channel or the region. The molecules that may be chemically attached to the portion of the channel or region include molecules that can electrostatically trap a species of interest (e.g., large, charged molecules with positive charge may be employed to trap $I^{3-}$ that gives rise to a brown colorimetric signal; sodium alginate may be employed to trap positively charged species), molecules (e.g., large molecules) that can create a complex and/or adduct with a species of interest, and others. Covalent cross-linking of the channel or region may comprise forming a covalent polymer network within the channel or region. This may be accomplished by the use of EDC/NHS chemistry, and/or through other methods.

Non-limiting examples of suitable types of physical functionalization include adding nanoparticles to the portion of the channel or region. The nanoparticles may fill some or all of the void volume in the portion of the channel or region, which may reduce the volume through which diffusion can occur. In some embodiments, the nanoparticles may be chemically functionalized (e.g., by one or more of the methods described above, by electrostatic charging). In some embodiments, the nanoparticles may comprise polystyrene.

The fluidic devices described herein may have one or more features of the fluidic devices described in the U.S. Provisional Application entitled "Patterned Dried Blood Spot Cards and Related Articles and Methods", filed on Jun. 22, 2018, incorporated herein by reference in its entirety. The fluidic devices described herein may have one or more features of the fluidic devices described in the International Application entitled "Patterned Dried Blood Spot Cards and Related Articles and Methods", filed on even date herewith, incorporated herein by reference in its entirety. The fluidic devices described herein may have one or more features of the fluidic devices described in International Patent Publication No. WO 2017/123668, filed on Jul. 20, 2017, and entitled "Separation of Cells Based on Size and Affinity Using Paper Microfluidic Device", incorporated herein by reference in its entirety.

The following examples are intended to illustrate certain embodiments of the present invention, but do not exemplify the full scope of the invention.

Example 1

This Example describes several different fluidic devices in which a fluid sample may be split into multiple portions which are then reacted at interfaces therebetween.

Figure 6A:
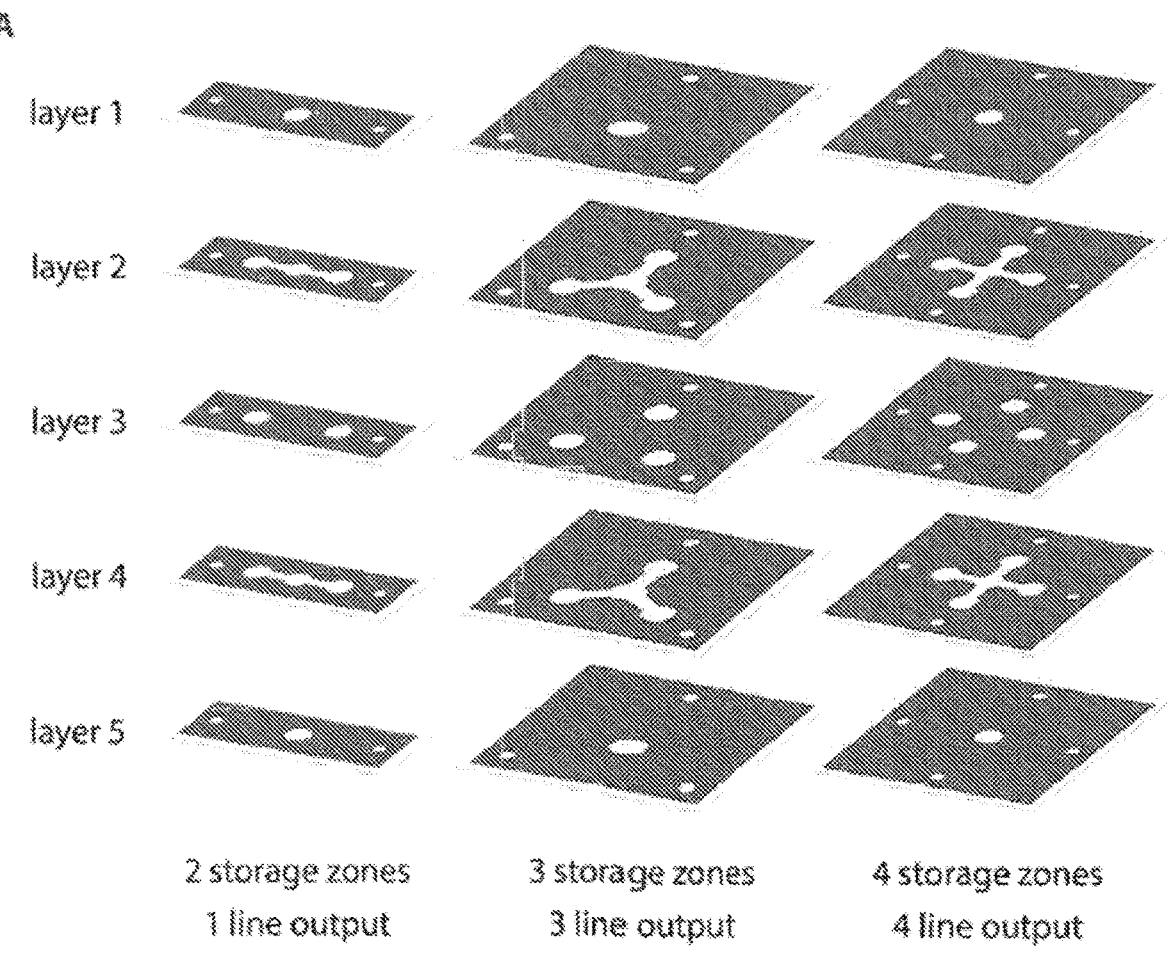
FIG. 6A shows schematic depiction of fluidic devices comprising five layers, according to some embodiments.
Figure 6B:
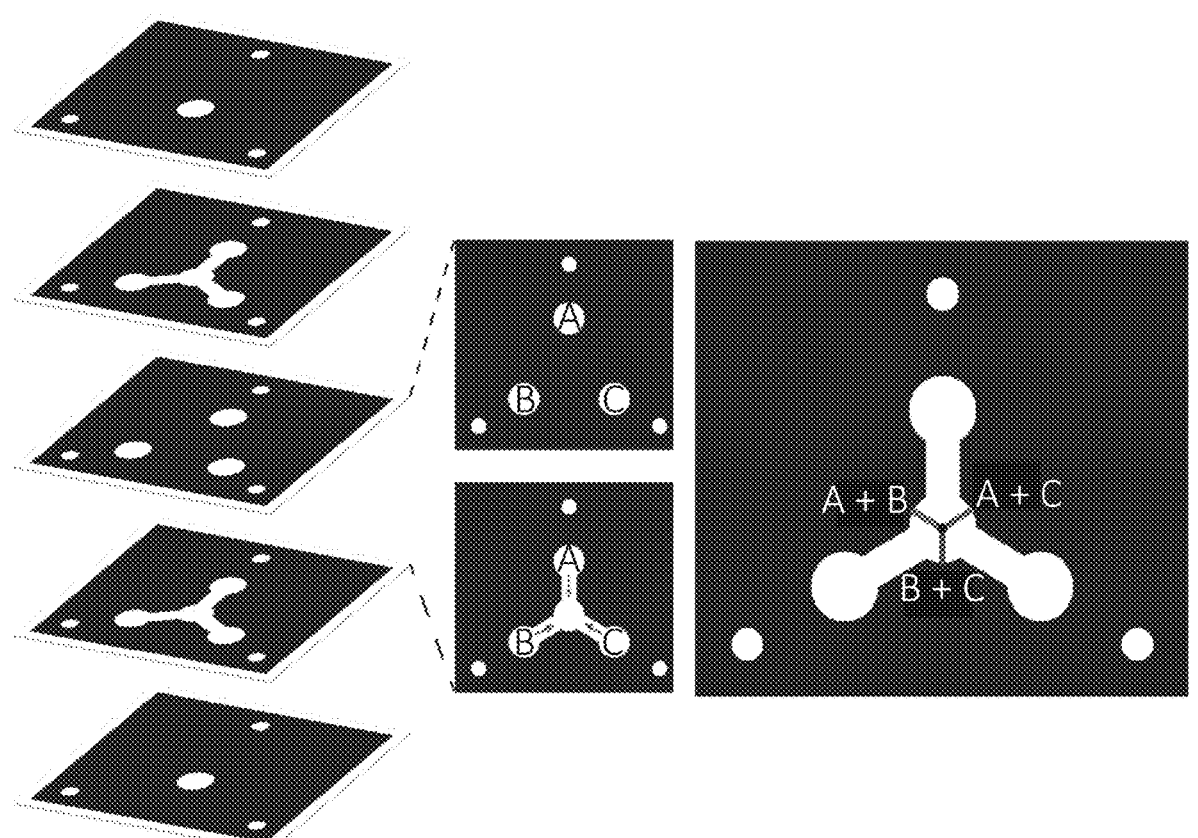
FIG. 6B shows a schematic depiction of a fluidic device comprising five layers and enlarged schematic depictions of two of the layers therein, according to some embodiments.
Figure 6C:
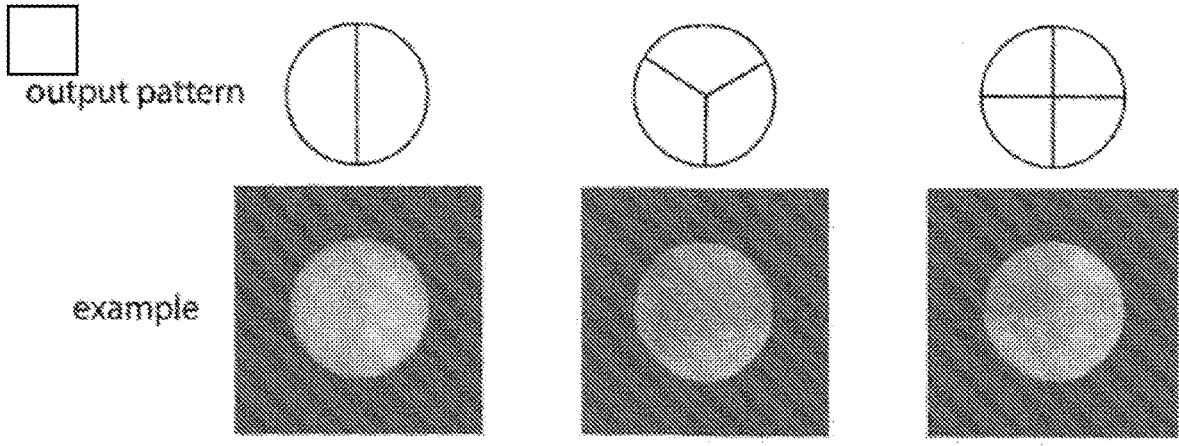
FIG. 6C shows predicted output patterns of the detection regions for several fluidic devices and photographs of the actual detection regions for those devices, according to some embodiments.
Figure 6D:
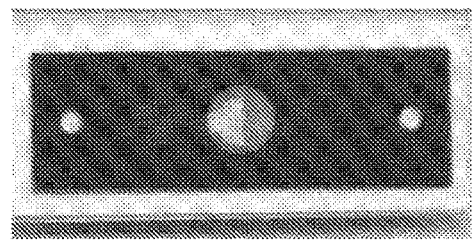
FIGS. 6D-6G show photographs of the detection regions of devices including differently-colored dyes in two disconnected regions within a layer, according to some embodiments.
Figure 6E:
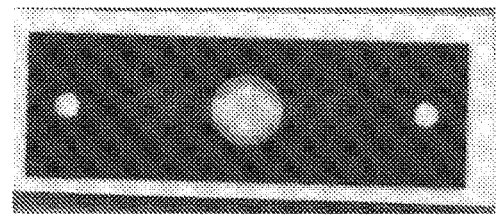
Figure 6F:
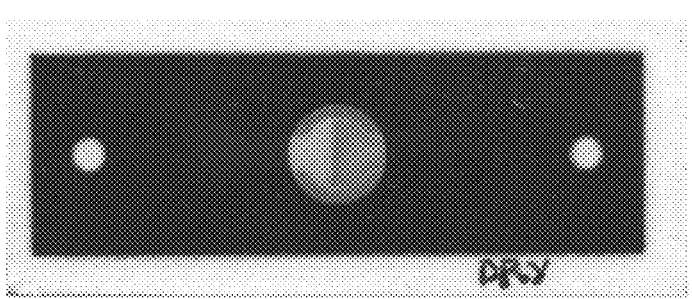
Figure 6G:
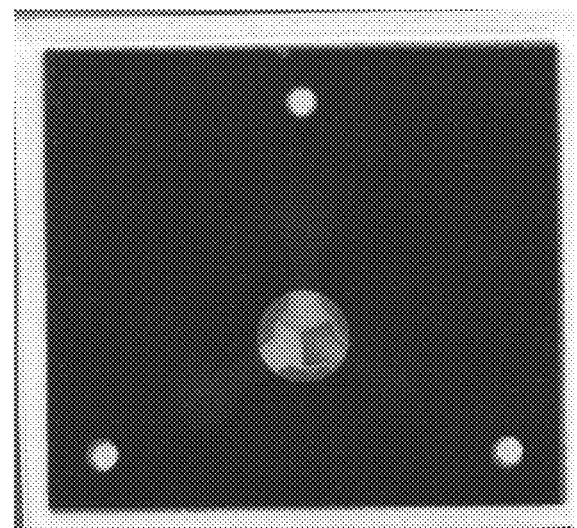
Figure 6H:
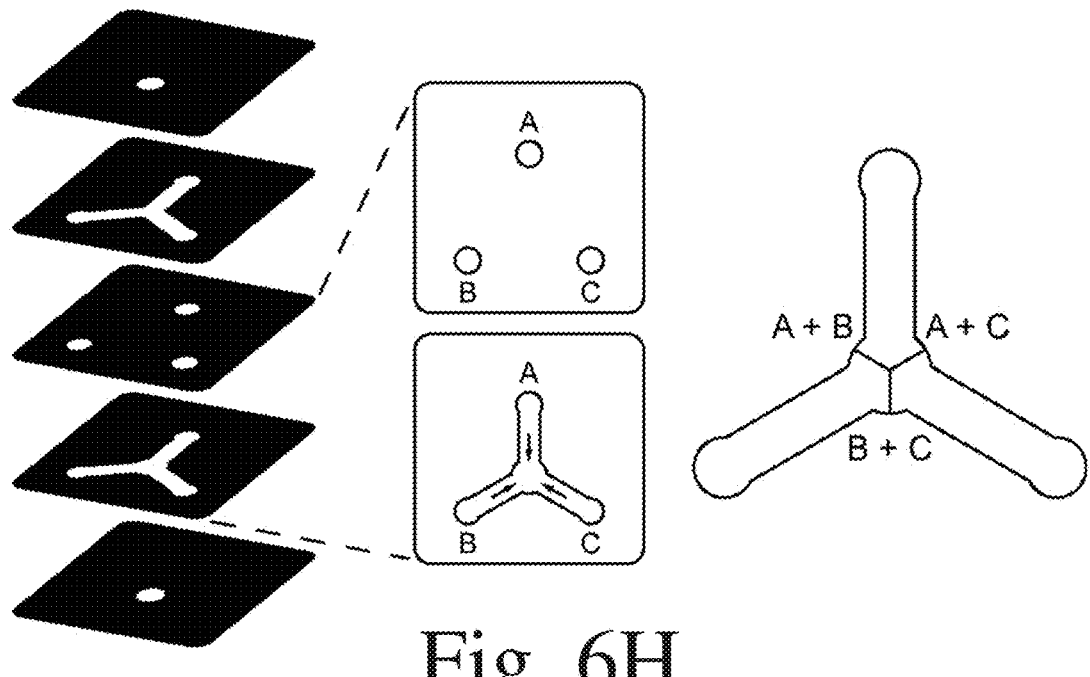
FIG. 6H shows a schematic depiction of a fluidic device comprising five layers and enlarged schematic depictions of two of the layers therein, according to some embodiments.

Three exemplary fluidic devices are shown in FIG. 6A. The devices shown in FIG. 6A include five paper layers. A fluid sample may be added to layer 1 and may then be distributed equally by channels 20 in layer 2 to form portions that flow into some number of disconnected regions 10 and 12 comprising stored reagents in layer 3. The sample may rehydrate the reagents stored in layer 3, with separate portions of the fluid sample rehydrating the reagents in different regions in layer 3. After rehydration, solutions of reagent and sample may be transported by channels 30 in layer 4 to a common reaction zone. Chemical reactions between the sample portions may occur at interfaces between the samples portions in layer 4 and fill the detection region 60 in layer 5. FIG. 6A shows several different channel geometries intended for different reagent storage requirements. Fluidic devices including these different channel geometries were fabricated, differently colored dyes were stored in each region in layer 3, and then water was flowed through the device from layer 1 to layer 5. FIGS. 6B and 6H show enlarged schematics of the device shown in the middle of FIG. 6A, and show how the different reagents stored in the different disconnected regions in layer 3 may react at interfaces between the three portions of the fluid sample in layer 4. FIG. 6C shows the predicted output patterns of the detection regions of each fluidic device and photographs of the actual detection regions for each device. FIGS. 6D-6G show photographs of the detection regions of other devices including differently-colored dyes in two disconnected regions in layer 3 (FIGS. 6D-6F) and three differently-colored dyes in three disconnected regions in layer 3 (FIG. 6G).

The device designs shown in FIGS. 6A-6G may restrict signal generation to a well-defined interface, which may allow for color intensity and/or line width to be related to analyte concentration.

Figure 7A:
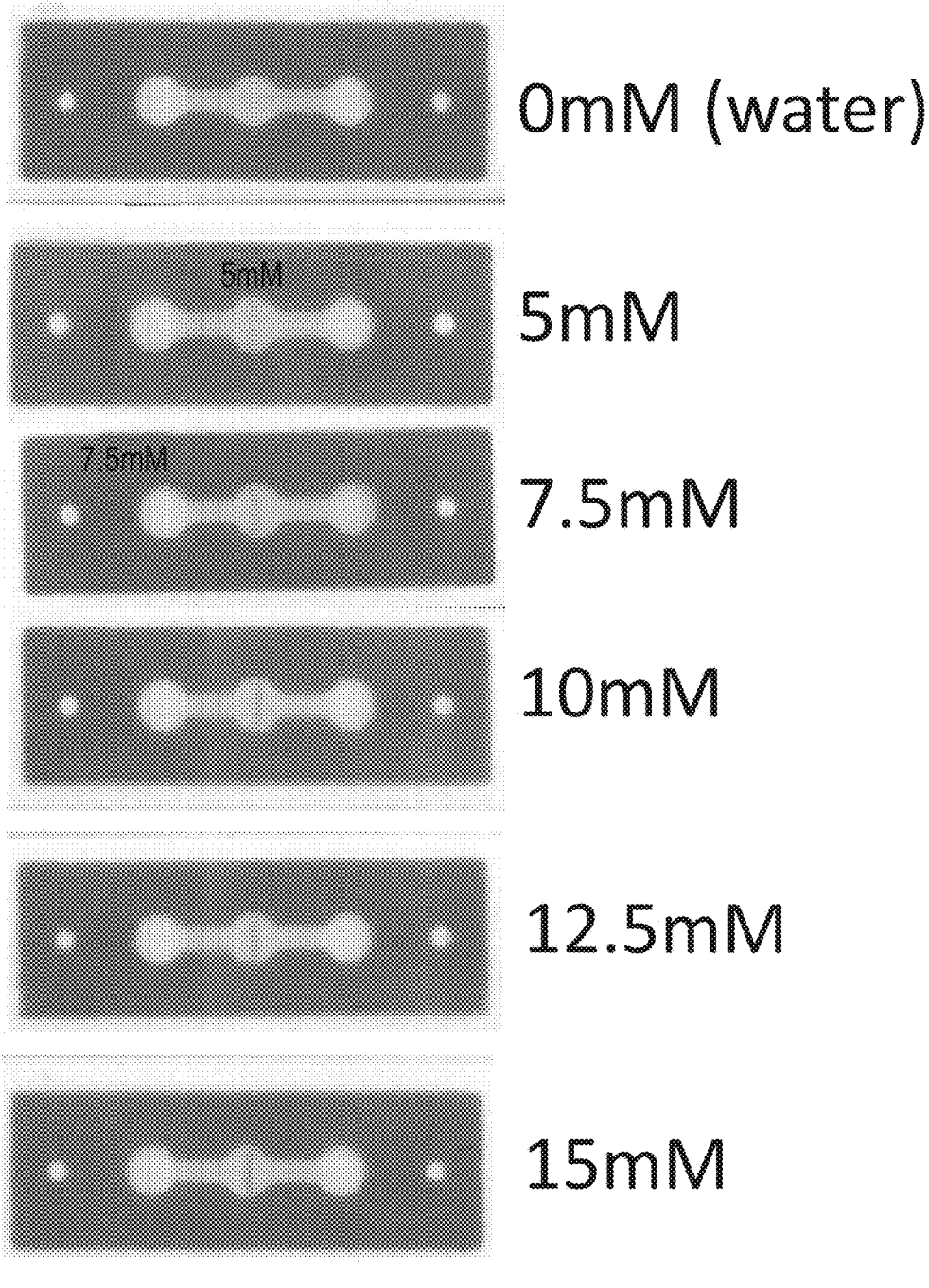
FIG. 7A shows layer 4 from various fluidic devices with the structure shown in the left hand sides of FIGS. 6A and 6C to which fluid samples including glucose in varying concentrations were added, according to some embodiments.
Figure 7B:
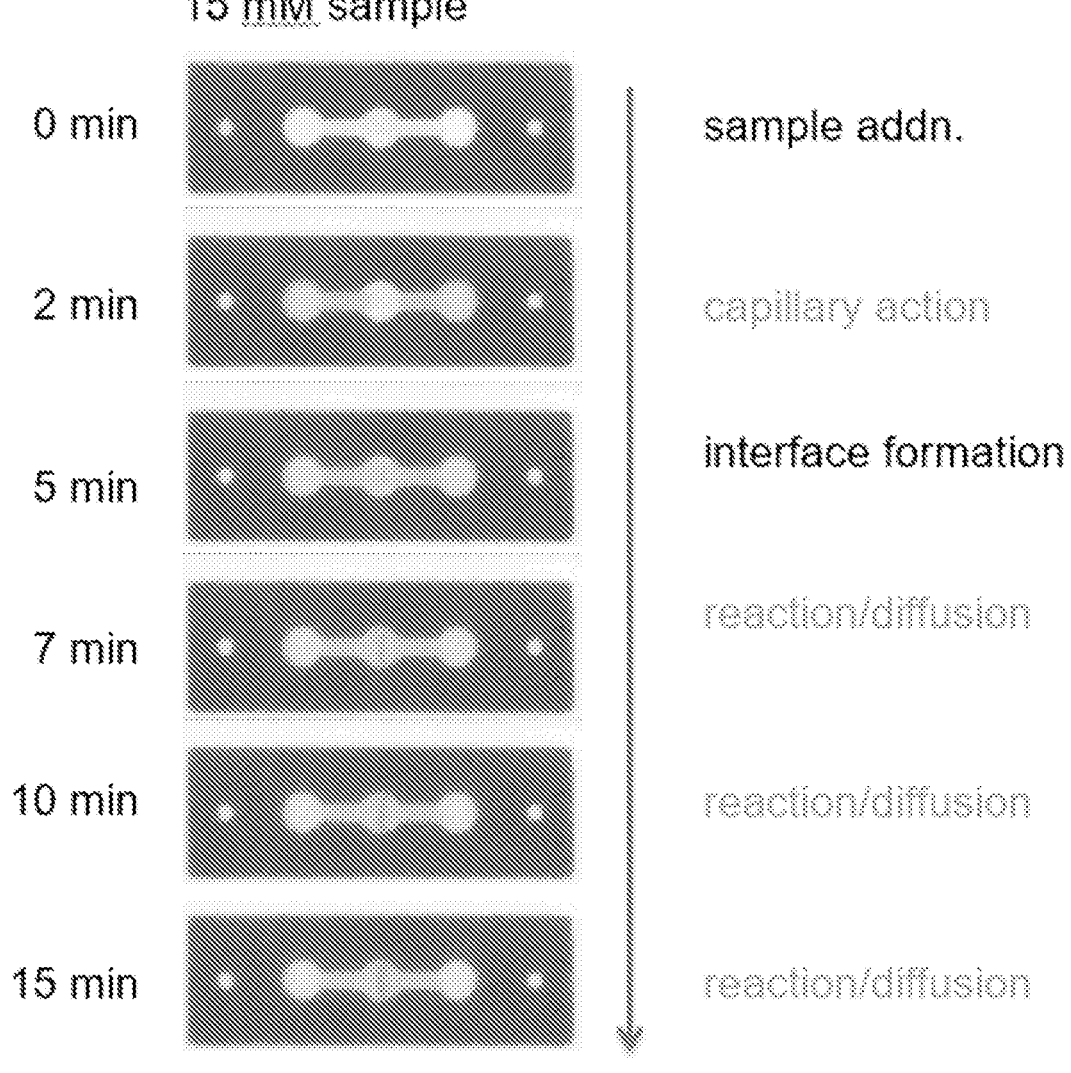
FIG. 7B shows layer 4 of a fluidic device with the structure shown in the left hand sides of FIGS. 6A and 6C, according to some embodiments.

The fluidic device shown in the left hand side of FIGS. 6A and 6C has also been used to detect a physiological concentration (10 mM) of glucose (FIGS. 7A-7B). Glucose oxidase and a mixture of potassium iodide and horseradish peroxidase were stored in disconnected regions in layer 3. When a glucose solution was introduced to the fluidic device in layer 1, a brown line was formed at the interface of the two advancing liquid fronts of the sample portions. FIG. 7A shows layer 4 from various fluidic devices with the structure shown in the left hand sides of FIGS. 6A and 6C to which fluid samples including glucose in varying concentrations were added. The photographs were taken 8 minutes after addition of the fluid samples. Fluid samples including more glucose formed signals of higher intensity than those including less glucose. FIG. 7B shows layer 4 of a fluidic device with the structure shown in the left hand sides of FIGS. 6A and 6C. To this device a fluid sample including 15 mM of glucose was added at various time points after fluid sample addition. A detectable signal had formed by 5 minutes after the fluid sample was added, which darkened and broadened as more time passed.

Figure 8A:
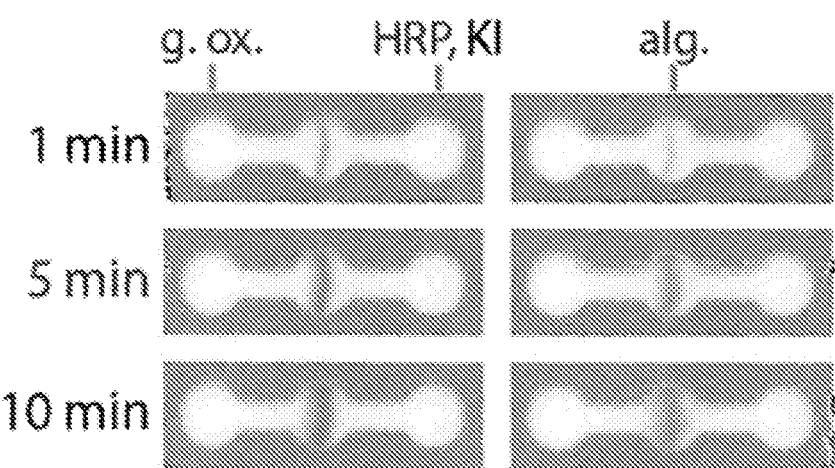
FIG. 8A shows layer 4 of an untreated fluidic device with the structure shown in the left hand sides of FIGS. 6A and 6C after addition of a fluid sample and shows layer 4 of a similar fluidic device that has been treated with a 1% solution of sodium alginate, according to some embodiments.
Figure 8B:
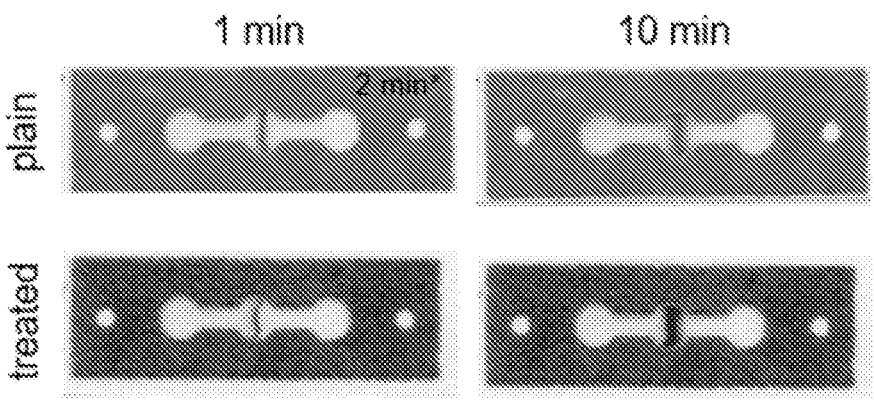
FIGS. 8B-8C show examples of signals formed in treated fluidic devices, according to some embodiments.
Figure 8C:
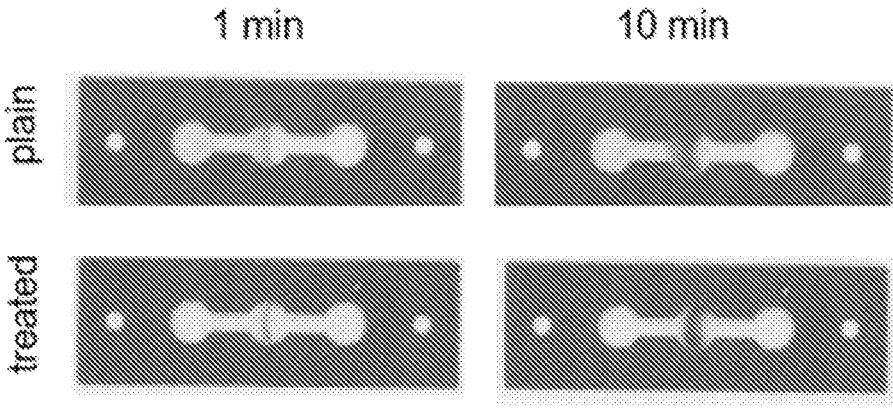

As shown in FIG. 7B, when fluidic devices fill, the signal can diffuse after formation. It may be possible to use chemical treatments and/or physical blockage of the paper's porous structure using nanoparticles to limit and/or eliminate signal diffusion after product formation. The left hand side of FIG. 8A shows layer 4 of an untreated fluidic device at three time points after addition of a fluid sample, and the right hand side of FIG. 8A shows layer 4 of a similar fluidic device that has been treated with a 1% solution of sodium alginate to promote retention of the signal at the initial interface between portions of the fluidic sample at these same time points. FIGS. 8B-8C show further examples of signals formed in treated fluidic devices. FIG. 8B shows a comparison between the signal formed in an untreated fluidic device (top) with that formed in a fluidic device treated with sodium alginate to promote retention of the signal at the initial interface between portions of the fluidic sample. For the devices shown in FIG. 8B, the ratio of the line width at 1 minute after fluid sample addition to the line width at 10 minutes after sample addition for the untreated fluidic device was 0.39, while that of the treated fluidic device was 0.33. FIG. 8C shows a comparison between the signal formed in an untreated fluidic device (top) with that formed in a fluidic device treated with 200 nm silica nanoparticles to promote retention of the signal at the initial interface between portions of the fluidic sample.

Example 2

This Example describes several different fluidic devices in which fluids may be reacted at interfaces therebetween and presents data from the operation of such devices.

Figure 9:
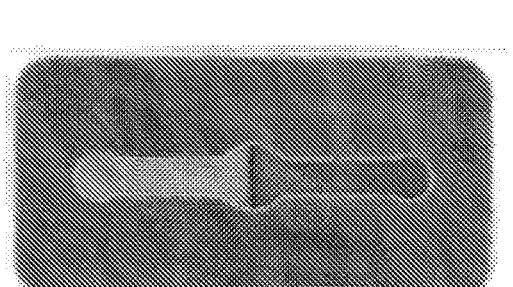
FIGS. 9-11 show three fluidic devices in which two or more fluids meet at interfaces therebetween, according to some embodiments.
Figure 10:
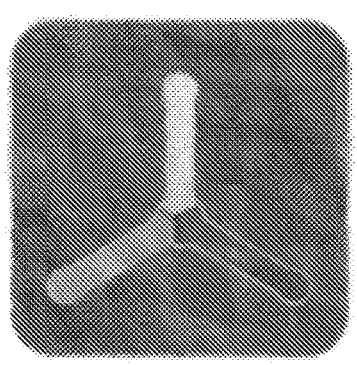
Figure 11:
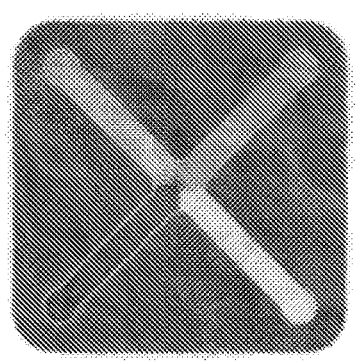

FIGS. 9-11 show three exemplary fluidic devices in which two or more fluids meet at interfaces therebetween. Each device shown in FIGS. 9-11 is a single layer fluidic device. The single layer is a Whatman 4 chromatography paper backed by a transparent laminating sheet. The paper also comprises wax printed therein and forming a barrier impermeable to fluid surrounding channels therein and fluid introduction regions therein. Each fluidic device comprises one or more channels with fluid introduction regions at its or their termini. For fluidic devices comprising three or more channels, the channels meet at a common intersection.

Solutions of different dyes in water were added to each of the sample introduction regions simultaneously by use of two pipettes (for the fluidic device shown in FIG. 9) or a custom-made multichannel pipette (for the fluidic devices shown in FIGS. 10-11). In FIG. 9, 4 µL of 1 mM erioglaucine in water was added to the left fluid introduction region, and 4 µL of 10 mM Allura Red in water was added to the right fluid introduction region. In FIG. 10, 3.5 µL of 40 mM tartrazine in water was added to the top fluid introduction region, 3.5 µL of 1 mM erioglaucine in water was added to the bottom left fluid introduction region, and 3.5 µL of 10 mM Allura Red in water was added to the bottom right fluid introduction region. In FIG. 11, 4.5 µL of 1 mM erioglaucine in water was added to the top left fluid introduction region, 4.5 µL of an aqueous solution comprising 1 mM erioglaucine disodium salt and 10 mM tartrazine was added to the top right fluid introduction region, 4.5 µL of 10 mM Allura Red in water was added to the bottom left fluid introduction region, and 4.5 µL of 40 mM tartrazine in water was added to the bottom right fluid introduction region.

Example 3

This Example describes the use of the fluidic device shown in FIG. 11 for the detection of iron(III) ions.

Figure 12:
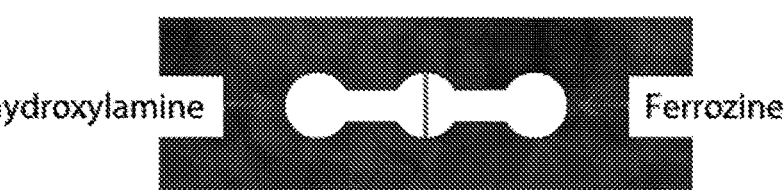
FIG. 12 shows a schematic depiction of a method of flowing two fluids towards each other to meet at an interface, according to some embodiments.
Figure 13:
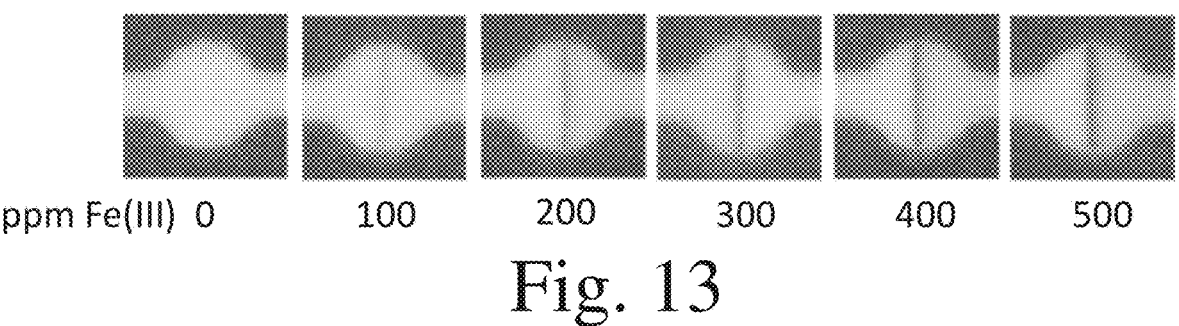
FIG. 13 shows photographs of the interface between a solution comprising hydroxylamine and a solution comprising ferrozine at varying initial levels of iron(III) initially present in the hydroxylamine solution, according to some embodiments.

Several experiments were performed, each in its own fluidic device. In each experiment, a solution comprising 0.1 g/mL of hydroxylamine in water and a known initial amount of iron(III) ions were added to one fluid introduction region of the multilayer fluidic device and a solution comprising 10 mg/mL of ferrozine in water was added to the other fluid introduction region. The two solutions flowed towards each other in the channel in fluidic communication with both fluid introduction regions and then met at an interface therein (as shown schematically in FIG. 12). Any iron(III) ions initially present in the solution comprising the hydroxylamine were reduced by the hydroxylamine to iron(II) ions. Upon meeting at the interface, the ferrozine reacted with any iron(II) ions in present in the solution comprising the hydroxylamine (e.g., iron(III) ions reduced to form iron(II) ions by the hydroxylamine), chelating it to form a magenta-colored signal at the interface. FIG. 13 shows photographs of the interface between the solution comprising the hydroxylamine and the solution comprising the ferrozine at varying initial levels of iron(III) initially present in the hydroxylamine solution. The photographs were taken approximately one minute after the samples were applied to the devices.

Example 4

This Example describes the use of the fluidic device shown in FIG. 11 for the detection of acetylcholinesterase.

Figure 14:
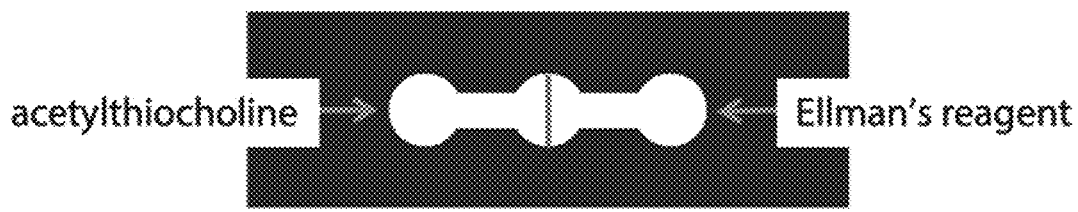
FIG. 14 shows a schematic depiction of a method of flowing two fluids towards each other to meet at an interface, according to some embodiments.
Figure 15:
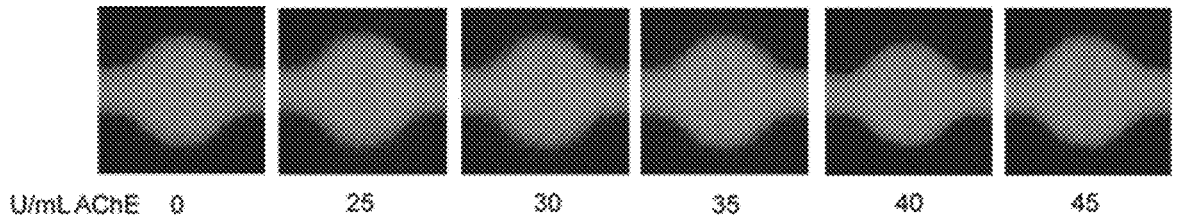
FIG. 15 shows photographs of the interface between a solution comprising acetylthiocholine and a solution comprising Ellman's reagent at varying levels of acetylcholinesterase present in the Ellman's reagent solution, according to some embodiments.

Several experiments were performed, each in its own fluidic device. In each experiment, a solution initially comprising 75 mM of acetylthiocholine chloride in water and a known amount of acetylcholinesterase were added to one fluid introduction region of the multilayer fluidic device and a solution comprising 30 mM of Ellman's reagent in phosphate buffer was added to the other fluid introduction region. The two solutions flowed towards each other in the channel in fluidic communication with both fluid introduction regions and then met at an interface therein (as shown schematically in FIG. 14). Any acetylcholinesterase in the solution comprising the acetylthiocholine converted a portion of the acetylthiocholine therein into thiocholine. Upon meeting at the interface, the Ellman's reagent reacted with any thiocholine present in the solution comprising the acetylthiocholine (e.g., acetylthiocholine reacted with the acetylcholinesterase to form thiocholine) to form a yellow reaction product at the interface. FIG. 15 shows photographs of the interface between the solution comprising the acetylthiocholine and the solution comprising the Ellman's reagent at varying levels of acetylcholinesterase present in the Ellman's reagent solution. The photographs were taken approximately two minutes after the samples were applied to the devices.

Example 5

This Example describes the design of fluidic devices that may be used to determine whether the concentration of the analyte in a fluid sample is above or below a known value.

Figure 16:
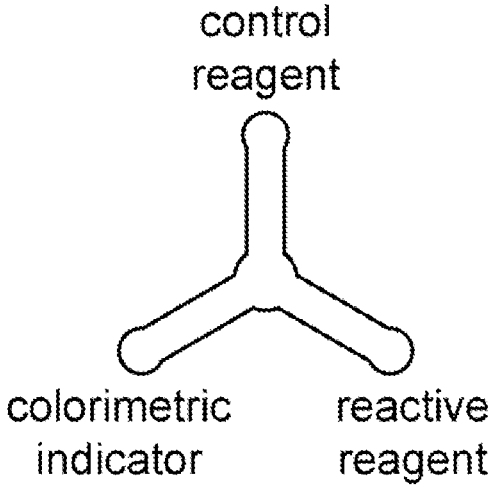
FIG. 16 shows a schematic depiction of a device comprising three channels that meet at a junction, according to some embodiments.

FIG. 16 shows a schematic depiction of a device having this property, which comprises three channels that meet at a junction: (1) A channel configured to contain a fluid sample having an unknown concentration of an analyte and a known concentration of a reagent configured to react with the analyte to produce a reaction product; (2) A channel configured to contain a fluid configured to react with the reaction product of the analyte to form a colored reaction product; and (3) A channel configured to contain a fluid having a known concentration of the reaction product of the analyte. Such devices may allow users thereof to compare the intensity at the interface between the fluids in the first and second channel with the intensity at the interface between the fluids in the second and third channels and determine thus whether the concentration of the reaction product of the analyte is above or below a known value (and accordingly whether the concentration of the analyte prior to reaction was above or below a known value).

Example 6

This Example describes the use of the fluidic device described in Example 5 to detect the concentration of iron(II) ions in a fluid sample.

Prior to the use of the fluidic devices to detect the concentration of iron(III) ions, each fluidic device was pretreated: 1 µL of a fluid comprising 100 mM of ascorbic acid in water was applied to the first channel, 1 µL of a solution comprising 5 mM of ferrozine in water was applied to the second channel, and 1 µL of a solution comprising 50 mM of iron(II) ions in water was applied to the third channel. These reagents were allowed to dry in these channels. Then, two experiments were performed. For each experiment, 2.8 µL of a fluid sample comprising a known initial concentration of iron(III) ions was introduced into each channel simultaneously with a custom pipette. The three portions of the fluid sample flowed towards the common junction point and formed interfaces therebetween. The fluidic devices were photographed within one minute of interface formation.

Figure 17:
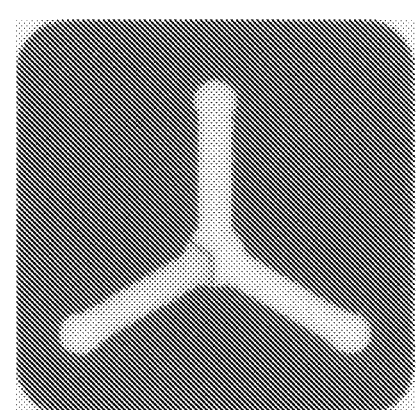
FIG. 17 shows a photograph of a fluidic device for which the fluid sample initially included 50 mM of iron(III) ions, according to some embodiments.
Figure 18:
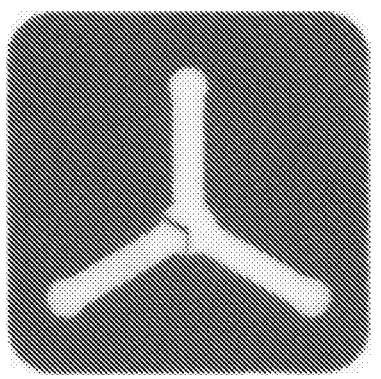
FIG. 18 shows a photograph of a fluidic device for which the fluid sample initially included 5 mM of iron(III) ions, according to some embodiments.

FIG. 17 shows a photograph of a fluidic device for which the fluid sample initially included 50 mM of iron(III) ions, and FIG. 18 shows a photograph of a fluidic device for which the fluid sample initially included 5 mM of iron(III) ions. In FIG. 17, the intensity and width of the color at the interface between the fluids in the first and second channels is the same as the intensity of the color at the interface between the fluids in the second and third channels due to the equivalent concentrations of iron(III) ions in both of these locations. In FIG. 18, the width of the color at the interface between the fluids in the first and second channels is much less than the intensity of the color at the interface between the fluids in the second and third channels due to the higher concentration of iron(III) ions in the third fluid than in the second fluid.

Example 7

This Example describes the use of the fluidic device described in Example 5 to detect the concentration of acetylcholinesterase in a fluid sample.

Prior to the use of the fluidic devices to detect the concentration of acetylcholinesterase, each fluidic device was pretreated: a fluid comprising 75 mM of acetylthiocholine chloride in water was applied to the first channel, a solution comprising 30 mM of Ellman's reagent in phosphate buffer was applied to the second channel, and a solution comprising 1 M of cysteine in water was applied to the third channel. These reagents were allowed to dry in these channels. Then, two experiments were performed. For each experiment, a fluid sample comprising a known concentration of acetylcholinesterase was introduced into each channel simultaneously with a custom pipette. The three portions of the fluid sample towards the common junction point and formed interfaces therebetween. The fluidic devices were photographed within two to three minutes of sample application.

Figure 19:
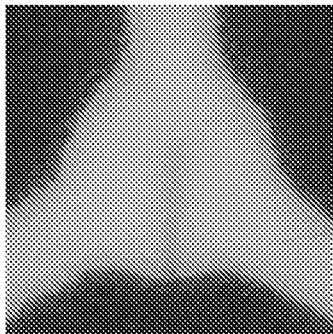
FIG. 19 shows a photograph of a fluidic device for which the fluid sample included 0 U/mL of acetylcholinesterase, according to some embodiments.
Figure 20:
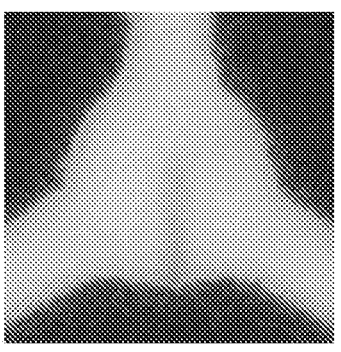
FIG. 20 shows a photograph of a fluidic device for which the fluid included 50 U/mL of acetylcholinesterase, according to some embodiments.

FIG. 19 shows a photograph of a fluidic device for which the fluid sample included 0 U/mL of acetylcholinesterase, and FIG. 20 shows a photograph of a fluidic device for which the fluid sample included 50 U/mL of acetylcholinesterase. In FIG. 19, there is hardly any color at the interface between the fluids in the first and second channels and appreciable color at the interface between the fluids in the second and third channels. This is indicative of the absence of thiocholine (and therefore the absence of acetylcholinesterase) in the fluid in the first channel. In FIG. 20, there is appreciable color at both the interfaces between the fluids in the first and second channels and the fluids in the second and third channels. This is indicative of the presence of an appreciable amount of thiocholine (and therefore acetylcholinesterase) in the fluid in the first channel.

Example 8

This Example describes two designs for multilayer fluidic devices.

Figure 21:
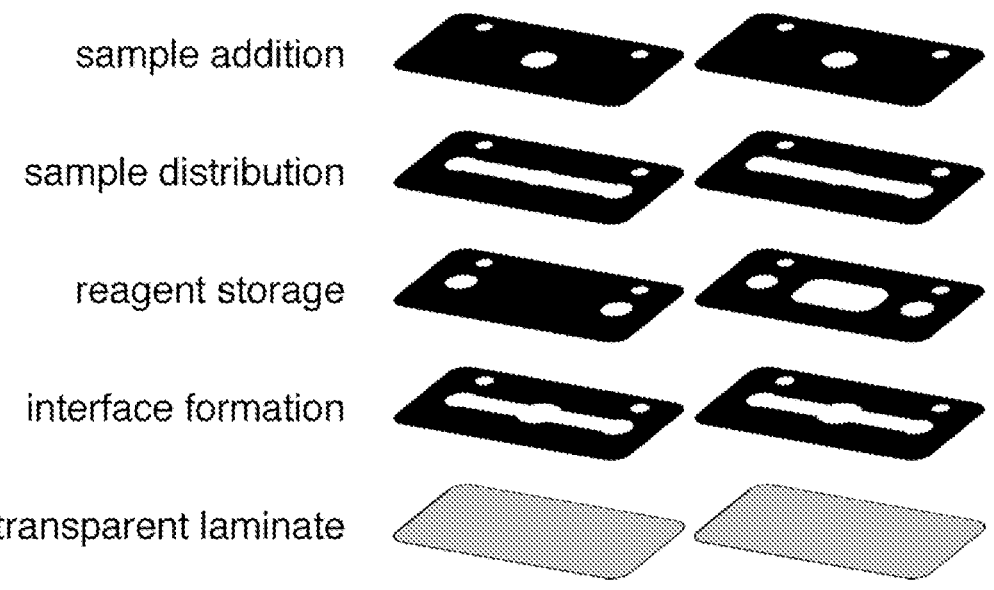
FIG. 21 shows exploded views of two multilayer fluidic devices, according to some embodiments.

Each multilayer fluidic device comprises a total of 5 layers of porous, absorbent materials (referred to below as paper layers) or cover layers. The narrative below describes the structure of each layer and how it is designed to interact with fluid samples introduced to the fluidic device. FIG. 21 shows exploded views of the multilayer fluidic devices.

Layer 1. A paper layer comprising a region configured to receive a fluid sample.

Layer 2. A paper layer comprising a channel in fluidic communication with the region configured to receive the fluidic sample in layer 1.

Layer 3. A paper layer comprising two disconnected regions in fluidic communication with the channel in layer 2.

Layer 4. A paper layer comprising a channel in fluidic communication with the disconnected regions in layer 3.

Layer 5. A cover layer that is a laminating sheet.

The multilayer fluidic devices shown in FIG. 21 are configured to receive a fluid sample, split it, and then recombine it. This may be accomplished by receiving the fluid sample at the region configured to receive the fluid sample in layer 1, flowing the fluid sample into layer 2, splitting the fluid sample into two portions by flowing it in two opposite directions in the channel in layer 2, flowing the two portions of the fluid sample into layer 3 and through the disconnected regions therein, flowing the two portions of the fluid sample into layer 4, and then recombining the two portions of the fluid sample by flowing them towards each other in the channel in layer 4. The disconnected regions in layer 3 may comprise reagents (the same or different), which may be solubilized by the fluid sample as it passes therethrough.

Figure 22:
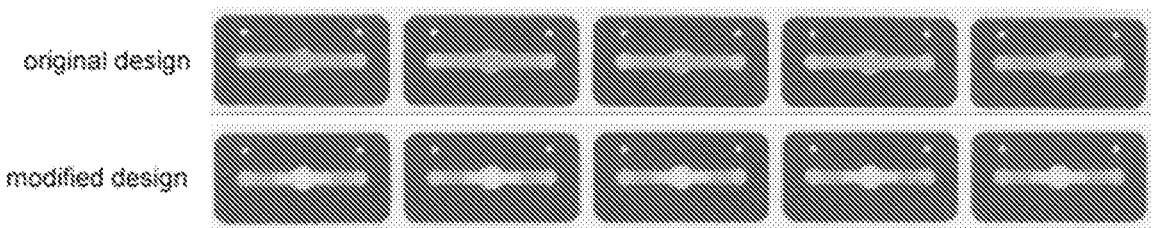
FIG. 22 shows photographs of five multilayer fluidic devices after a water sample has been added thereto and flowed therethrough, according to some embodiments.

For the multilayer fluidic device shown on the left of FIG. 21, all portions of each paper layer other than regions configured to receive a fluid sample, channels, disconnected regions, and regions allowing for alignment of the layers comprise an opaque wax that is impermeable to fluids with which the device is configured for use. The multilayer fluidic device shown on the right of FIG. 21 differs from the multilayer fluidic device shown on the left of FIG. 21 because it further comprises a region in the center of layer 3 that is not in fluidic communication with either of the disconnected regions therein and that lacks the opaque wax. The disconnected region is also not in fluidic communication with the channels in the layers above and below because there is an optically transparent double-sided adhesive positioned therebetween. This design is believed to be advantageous for multilayer fluidic devices that are configured to be flipped over prior to being detection of one or more features thereof. The region in the center of layer 3 that lacks the opaque wax is believed to provide a brighter background upon which any reaction at an interface between the two portions of the fluid sample added to the device may be viewed. FIG. 22 shows photographs of five multilayer fluidic devices having each structure after a water sample has been added thereto and flowed therethrough. This Fig. evidences the brighter background of the multilayer fluidic devices including the region in the center of layer 3 in comparison to the multilayer fluidic devices lacking the region in the center of layer 3.

Example 9

This Example compares multilayer fluidic devices comprising paper layers having different average pore sizes.

Three devices having the structure shown on the right side of FIG. 21 and suitable for performing a lactate assay were fabricated, each including a layer 4 having a paper layer with a different average pore size. These average pore sizes were 2.5 microns, 15 microns, and 25 microns. The left reagent storage region of each device comprised 3-(4,5-dimethyl-thiazol-2-yl)-2,5-diphenyltetrazolium bromide (MTT), 1-methoxy-5-methylphenazinium methylsulfate (PMS), and TRIS buffer. The right reagent storage region of each device comprised lactate dehydrogenase, β-nicotinamide adenine dinucleotide ($NAD^+$), and hydrazine buffer. Without wishing to be bound by any particular theory, it is believed that, upon addition of a fluid sample that comprises lactate to the device, the lactate in the fluid sample will reduce $NAD^+$ to NADH. It is also believed that this NADH will react with MTT in the presence of PMS to form formazan. Formazan is an electron-transport mediator that forms a purpose color.

Figure 23:
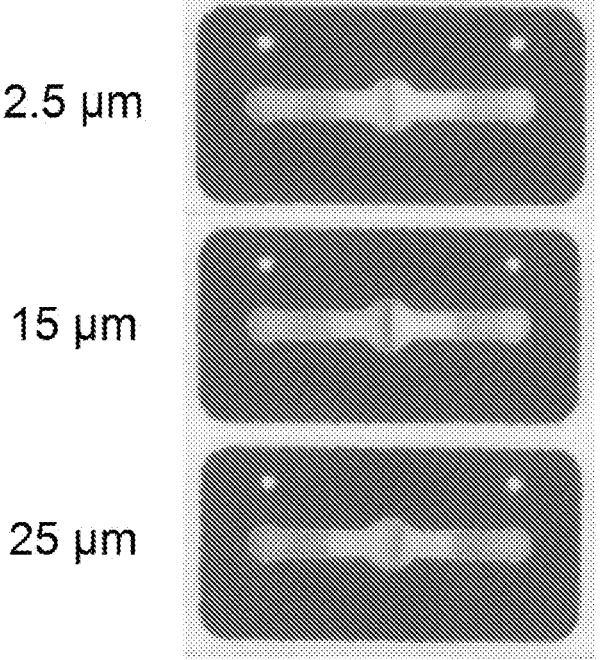
FIG. 23 shows photographs of multilayer fluidic devices after the addition of a fluid sample thereto, according to some embodiments.

FIG. 23 shows the devices 15 minutes after the addition of a fluid sample thereto, in which the line at the interface between the split portions of the fluid sample is due to formazan. As shown in FIG. 23, the signal formed in the paper layers having 2.5 micron and 15 micron average pore sizes has a smaller width than the signal formed in the paper layer having a 25 micron average pore size.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A fluidic device, comprising:
a first layer comprising first and second regions;
a second layer comprising a first channel; and
a third layer comprising a second channel in fluidic communication with the first and second regions, wherein:
the first channel directly fluidically connects the first and second regions;
the second channel directly fluidically connects the first and second regions;
the first layer is disposed on the second layer;
the third layer is disposed on the first layer;

the first and second regions are disconnected from each other in the first layer;
at least one of the first layer, second layer, and third layer comprises a porous material;
the first channel is in fluidic communication with the second channel via the first region and via the second region;
the first channel is positioned on both the first region and the second region; and
the second channel is positioned on both the first region and the second region.

2. The fluidic device of claim 1, wherein the fluidic device comprises a fourth layer disposed on the third layer.

3. The fluidic device of claim 2, wherein the fourth layer comprises a central region in fluidic communication with an environment external to the fluidic device.

4. The fluidic device of claim 3, wherein the central region in fluidic communication with the environment external to the fluidic device is positioned directly above the first channel.

5. The fluidic device of claim 2, wherein the fluidic device comprises a fifth layer, and wherein the third layer is disposed on the fifth layer.

6. The fluidic device of claim 5, wherein the fifth layer comprises a detection region in fluidic communication with the second channel.

7. The fluidic device of claim 6, wherein the detection region is positioned directly below the first channel.

8. The fluidic device of claim 1, wherein the first and second regions are directly above the second channel.

9. The fluidic device of claim 1, wherein the first channel is directly above the first and second regions.

10. The fluidic device of claim 1, wherein the first and second regions are not in fluidic communication with each other through the first layer.

11. The fluidic device of claim 1, wherein the first channel and second channel are not in fluidic communication with each other other than through the first and second regions.

12. The fluidic device of claim 1, wherein the first layer comprises a first porous material, wherein the second layer comprises a second porous material, wherein the third layer comprises a third porous material, and wherein the first, second, and third porous materials are the same.

13. The fluidic device of claim 1, wherein the porous material is absorbent.

14. A fluidic device, comprising:
a first layer comprising first and second regions;
a second layer comprising a single first channel; and
a third layer comprising a single second channel in fluidic communication with the first and second regions, wherein:
the first layer is disposed on the second layer;
the third layer is disposed on the first layer;
the first and second regions are disconnected from each other in the first layer;
the first and second regions are in fluidic communication with the first channel;
at least one of the first layer, second layer, and third layer comprises a porous material;
the first channel is in fluidic communication with the second channel via the first region and via the second region;
the first channel is positioned on both the first region and the second region; and
the second channel is positioned on both the first region and the second region.

15. The fluidic device of claim 14, wherein the fluidic device comprises a fourth layer disposed on the third layer.

16. The fluidic device of claim 15, wherein the fourth layer comprises a central region in fluidic communication with an environment external to the fluidic device.

17. The fluidic device of claim 16, wherein the central region in fluidic communication with the environment external to the fluidic device is positioned directly above the first channel.

18. The fluidic device of claim 15, wherein the fluidic device comprises a fifth layer, and wherein the third layer is disposed on the fifth layer.

19. The fluidic device of claim 18, wherein the fifth layer comprises a detection region in fluidic communication with the second channel.

20. The fluidic device of claim 14, wherein the porous material is absorbent.

\* \* \* \* \*